US012779194B2

(12) United States Patent
Okarski et al.

(10) Patent No.: US 12,779,194 B2
(45) Date of Patent: Nov. 3, 2026

(54) ELECTRODE ASSEMBLIES OF A BASKET CATHETER HAVING MECHANICAL RETAINERS AND METHODS OF THE SAME

(71) Applicant: Biosense Webster (Israel) Ltd., Yokneam (IL)

(72) Inventors: Kevin Mark Okarski, Monrovia, CA (US); Keshava Datta, Chino Hills, CA (US); Abubakarr Bah, Irvine, CA (US); Thanh Nguyen, El Monte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 827 days.

(21) Appl. No.: 18/066,117

(22) Filed: Dec. 14, 2022

(65) Prior Publication Data

US 2023/0226336 A1 Jul. 20, 2023

Related U.S. Application Data

(60) Provisional application No. 63/301,146, filed on Jan. 20, 2022.

(51) Int. Cl.
*A61M 39/10* (2006.01)
*A61B 18/00* (2006.01)

(52) U.S. Cl.
CPC ... *A61M 39/10* (2013.01); *A61B 2018/00577* (2013.01)

(58) Field of Classification Search
CPC .............. A61M 39/10; A61M 25/0074; A61M 25/0024; A61M 25/10; A61B 2018/00577;

(Continued)

(56) References Cited

U.S. PATENT DOCUMENTS 3,952,747 A 4/1976 Kimmell, Jr.
4,699,147 A 10/1987 Chilson et al.

(Continued)

FOREIGN PATENT DOCUMENTS

CN 105761835 A 7/2016
CN 111248993 A 6/2020

(Continued)

OTHER PUBLICATIONS

Extended European Search Report and Opinion dated Jun. 15, 2023, from corresponding European Application No. 23152482.8.

(Continued)

*Primary Examiner* — Lauren P Farrar

(57) ABSTRACT

The disclosed technology includes a medical probe including a tubular shaft having an expandable basket assembly coupled to a distal end of the tubular shaft. The basket assembly can have at least one spine extending along a longitudinal axis and configured to bow radially outward from the longitudinal axis when the basket assembly is transitioned from a collapsed form to an expanded form. The basket assembly can include electrode assemblies each attached to the spine. Each electrode assembly includes an electrode and a first and second electrically insulating portion that electrically isolate the electrode from the spine. The electrode, the first electrically insulating portion, and the second electrically insulating portion are interlocked onto the spine such that the plurality of electrode assemblies are prevented from sliding proximally or distally along a length of the spine.

18 Claims, 15 Drawing Sheets

(58) Field of Classification Search
CPC .................. A61B 5/287; A61B 5/6858; A61B 2018/00029; A61B 2018/0016; A61B 2018/00267; A61B 2018/00357; A61B 2018/00613; A61B 2018/1405; A61B 2218/002; A61B 18/1492
See application file for complete search history.

(56) References Cited

U.S. PATENT DOCUMENTS 4,940,064 A 7/1990 Desai
5,215,103 A 6/1993 Desai
5,255,679 A 10/1993 Imran
5,293,869 A 3/1994 Edwards et al.
5,309,910 A 5/1994 Edwards et al.
5,313,943 A 5/1994 Houser et al.
5,324,284 A 6/1994 Imran
5,345,936 A 9/1994 Pomeranz et al.
5,365,926 A 11/1994 Desai
5,396,887 A 3/1995 Imran
5,400,783 A 3/1995 Pomeranz et al.
5,411,025 A 5/1995 Webster, Jr.
5,415,166 A 5/1995 Imran
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,681,280 A 10/1997 Rusk et al.
5,718,241 A 2/1998 Ben-Haim et al.
5,722,401 A 3/1998 Pietroski et al.
5,722,403 A 3/1998 McGee et al.
5,725,525 A 3/1998 Kordis
5,730,128 A 3/1998 Pomeranz et al.
5,772,590 A 6/1998 Webster, Jr.
5,782,239 A 7/1998 Webster, Jr.
5,782,899 A 7/1998 Imran
5,823,189 A 10/1998 Kordis
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,944,022 A 8/1999 Nardella et al.
5,968,040 A 10/1999 Swanson et al.
5,983,126 A 11/1999 Wittkampf
6,014,579 A 1/2000 Pomeranz et al.
6,014,590 A 1/2000 Whayne et al.
6,023,638 A 2/2000 Swanson
6,119,030 A 9/2000 Morency
6,198,974 B1 3/2001 Webster, Jr.
6,216,043 B1 4/2001 Swanson et al.
6,216,044 B1 4/2001 Kordis
6,428,537 B1 8/2002 Swanson et al.
6,456,864 B1 9/2002 Swanson et al.
6,484,118 B1 11/2002 Govari
6,574,492 B1 6/2003 Ben-Haim et al.
6,584,345 B2 6/2003 Govari
6,600,948 B2 7/2003 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,837,886 B2 1/2005 Collins et al.
6,866,662 B2 3/2005 Fuimaono et al.
6,892,091 B1 5/2005 Ben-Haim et al.
6,970,730 B2 11/2005 Fuimaono et al.
6,973,340 B2 12/2005 Fuimaono et al.
6,980,858 B2 12/2005 Fuimaono et al.
6,987,995 B2 1/2006 Drysen
7,048,734 B1 5/2006 Fleischman et al.
7,142,903 B2 11/2006 Rodriguez et al.
7,149,563 B2 12/2006 Fuimaono et al.
7,255,695 B2 8/2007 Falwell et al.
7,257,434 B2 8/2007 Fuimaono et al.
7,274,957 B2 9/2007 Drysen
7,377,906 B2 5/2008 Selkee
7,399,299 B2 7/2008 Daniel et al.
7,410,486 B2 8/2008 Fuimaono et al.
7,522,950 B2 4/2009 Fuimaono et al.
7,591,799 B2 9/2009 Selkee
7,593,760 B2 9/2009 Rodriguez et al.
RE41,334 E 5/2010 Beatty et al.
7,720,517 B2 5/2010 Drysen
7,794,473 B2 9/2010 Tessmer et al.
7,846,157 B2 12/2010 Kozel
7,853,302 B2 12/2010 Rodriguez et al.
7,930,018 B2 4/2011 Harlev et al.
8,000,765 B2 8/2011 Rodriguez et al.
8,007,495 B2 8/2011 McDaniel et al.
8,021,327 B2 9/2011 Selkee
8,048,063 B2 11/2011 Aeby et al.
8,103,327 B2 1/2012 Harlev et al.
8,167,845 B2 5/2012 Wang et al.
8,224,416 B2 7/2012 De La Rama et al.
8,235,988 B2 8/2012 Davis et al.
8,275,440 B2 9/2012 Rodriguez et al.
8,295,902 B2 10/2012 Salahieh et al.
8,346,339 B2 1/2013 Kordis et al.
8,357,152 B2 1/2013 Govari et al.
8,435,232 B2 5/2013 Aeby et al.
8,447,377 B2 5/2013 Harlev et al.
8,475,450 B2 7/2013 Govari et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,567,265 B2 10/2013 Aeby et al.
8,712,550 B2 4/2014 Grunewald
8,728,065 B2 5/2014 Fish et al.
8,755,861 B2 6/2014 Harlev et al.
8,825,130 B2 9/2014 Just et al.
8,906,011 B2 12/2014 Gelbart et al.
8,945,120 B2 2/2015 McDaniel et al.
8,979,839 B2 3/2015 De La Rama et al.
9,037,264 B2 5/2015 Just et al.
9,131,980 B2 9/2015 Bloom
9,204,929 B2 12/2015 Solis
9,277,960 B2 3/2016 Weinkam et al.
9,314,208 B1 4/2016 Altmann et al.
9,339,331 B2 5/2016 Tegg et al.
9,486,282 B2 11/2016 Solis
9,554,718 B2 1/2017 Bar-Tal et al.
D782,686 S 3/2017 Werneth et al.
9,585,588 B2 3/2017 Marecki et al.
9,597,036 B2 3/2017 Aeby et al.
9,687,297 B2 6/2017 Just et al.
9,693,733 B2 7/2017 Altmann et al.
9,782,099 B2 10/2017 Williams et al.
9,788,895 B2 10/2017 Solis
9,801,681 B2 10/2017 Laske et al.
9,814,618 B2 11/2017 Nguyen et al.
9,833,161 B2 12/2017 Govari
9,848,795 B2 12/2017 Marecki et al.
9,894,756 B2 2/2018 Weinkam et al.
9,895,073 B2 2/2018 Solis
9,907,609 B2 3/2018 Cao et al.
9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,045,707 B2 8/2018 Govari
10,078,713 B2 9/2018 Auerbach et al.
10,111,623 B2 10/2018 Jung et al.

(56) References Cited

U.S. PATENT DOCUMENTS 10,130,420 B2 11/2018 Basu et al.
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.
10,231,328 B2 3/2019 Weinkam et al.
10,238,309 B2 3/2019 Bar-Tal et al.
10,278,590 B2 5/2019 Salvestro et al.
D851,774 S 6/2019 Werneth et al.
10,314,505 B2 6/2019 Williams et al.
10,314,507 B2 6/2019 Govari et al.
10,314,648 B2 6/2019 Ge et al.
10,314,649 B2 6/2019 Bakos et al.
10,342,608 B2 7/2019 Wang et al.
10,349,855 B2 7/2019 Zeidan et al.
10,350,003 B2 7/2019 Weinkam et al.
10,362,991 B2 7/2019 Tran et al.
10,375,827 B2 8/2019 Weinkam et al.
10,376,170 B2 8/2019 Quinn et al.
10,376,221 B2 8/2019 Iyun et al.
10,398,348 B2 9/2019 Osadchy et al.
10,403,053 B2 9/2019 Katz et al.
10,441,188 B2 10/2019 Katz et al.
10,470,682 B2 11/2019 Deno et al.
10,470,714 B2 11/2019 Altmann et al.
10,482,198 B2 11/2019 Auerbach et al.
10,492,857 B2 12/2019 Guggenberger et al.
10,542,620 B2 1/2020 Weinkam et al.
10,575,743 B2 3/2020 Basu et al.
10,575,745 B2 3/2020 Solis
10,582,871 B2 3/2020 Williams et al.
10,582,894 B2 3/2020 Ben Zrihem et al.
10,596,346 B2 3/2020 Aeby et al.
10,602,947 B2 3/2020 Govari et al.
10,617,467 B2 4/2020 Viswanathan et al.
10,617,867 B2 4/2020 Viswanathan et al.
10,660,702 B2 5/2020 Viswanathan et al.
10,667,753 B2 6/2020 Werneth et al.
10,674,929 B2 6/2020 Houben et al.
10,681,805 B2 6/2020 Weinkam et al.
10,682,181 B2 6/2020 Cohen et al.
10,687,892 B2 6/2020 Long et al.
10,688,278 B2 6/2020 Beeckler et al.
10,702,178 B2 7/2020 Dahlen et al.
10,716,477 B2 7/2020 Salvestro et al.
10,758,304 B2 9/2020 Aujla
10,765,371 B2 9/2020 Hayam et al.
10,772,566 B2 9/2020 Aujila
10,799,281 B2 10/2020 Goertzen et al.
10,842,558 B2 11/2020 Harlev et al.
10,842,561 B2 11/2020 Viswanathan et al.
10,863,914 B2 12/2020 Govari et al.
10,881,376 B2 1/2021 Shemesh et al.
10,898,139 B2 1/2021 Guta et al.
10,905,329 B2 2/2021 Bar-Tal et al.
10,912,484 B2 2/2021 Ziv-Ari et al.
10,918,306 B2 2/2021 Govari et al.
10,939,871 B2 3/2021 Altmann et al.
10,952,795 B2 3/2021 Cohen et al.
10,973,426 B2 4/2021 Williams et al.
10,973,461 B2 4/2021 Baram et al.
10,987,045 B2 4/2021 Basu et al.
11,006,902 B1 5/2021 Bonyak et al.
11,040,208 B1 6/2021 Govari et al.
11,045,628 B2 6/2021 Beeckler et al.
11,051,877 B2 7/2021 Sliwa et al.
11,071,585 B2 7/2021 Zhang et al.
11,109,788 B2 9/2021 Rottmann et al.
11,116,435 B2 9/2021 Urman et al.
11,129,574 B2 9/2021 Cohen et al.
11,160,482 B2 11/2021 Solis
11,164,371 B2 11/2021 Yellin et al.
2002/0198522 A1 12/2002 Kordis et al.
2004/0210121 A1 10/2004 Fuimaono et al.
2006/0009689 A1 1/2006 Fuimaono et al.
2006/0009690 A1 1/2006 Fuimaono et al.
2006/0058813 A1 3/2006 Teague et al.
2006/0100669 A1 5/2006 Fuimaono et al.
2007/0093806 A1 4/2007 Desai et al.
2007/0276212 A1 11/2007 Fuimaono et al.
2008/0234564 A1 9/2008 Beatty et al.
2009/0149848 A1 6/2009 Werneth et al.
2010/0063478 A1 3/2010 Selkee
2011/0118726 A1 5/2011 De La Rama et al.
2011/0160574 A1 6/2011 Harlev et al.
2011/0190625 A1 8/2011 Harlev et al.
2011/0245756 A1 10/2011 Arora et al.
2011/0301597 A1 12/2011 McDaniel et al.
2012/0271136 A1 10/2012 Kordis et al.
2012/0271138 A1 10/2012 Kordis et al.
2012/0271140 A1 10/2012 Kordis et al.
2013/0090651 A1 4/2013 Smith
2013/0150693 A1 6/2013 D'Angelo
2013/0172715 A1 7/2013 Just et al.
2013/0172872 A1 7/2013 Subramaniam et al.
2013/0172883 A1 7/2013 Lopes et al.
2013/0178850 A1 7/2013 Lopes et al.
2013/0190587 A1 7/2013 Lopes et al.
2013/0296852 A1 11/2013 Madjarov et al.
2014/0025069 A1 1/2014 Willard et al.
2014/0052118 A1 2/2014 Laske et al.
2014/0088588 A1 3/2014 Jarrad
2014/0180147 A1 6/2014 Thakur et al.
2014/0180151 A1 6/2014 Maskara et al.
2014/0180152 A1 6/2014 Maskara et al.
2014/0257069 A1 9/2014 Eliason et al.
2014/0276712 A1 9/2014 Mallin et al.
2014/0276746 A1 9/2014 Nabutovsky et al.
2014/0288552 A1 9/2014 Kunis
2014/0309512 A1 10/2014 Govari et al.
2014/0309513 A1 10/2014 Fish et al.
2014/0350551 A1 11/2014 Raatikka et al.
2015/0011991 A1 1/2015 Buysman et al.
2015/0045863 A1 2/2015 Litscher et al.
2015/0080693 A1 3/2015 Solis
2015/0105770 A1 4/2015 Amit
2015/0119878 A1 4/2015 Heisel et al.
2015/0133919 A1 5/2015 McDaniel et al.
2015/0208942 A1 7/2015 Bar-Tal et al.
2015/0223757 A1 8/2015 Werneth et al.
2015/0250424 A1 9/2015 Govari et al.
2015/0270634 A1 9/2015 Buesseler et al.
2015/0282859 A1 10/2015 Bencn et al.
2015/0342491 A1 12/2015 Marecki et al.
2015/0342532 A1 12/2015 Basu et al.
2015/0351625 A1 12/2015 Schroth et al.
2015/0366508 A1* 12/2015 Chou ..................... A61N 1/056
600/467
2016/0081746 A1 3/2016 Solis
2016/0113582 A1 4/2016 Altmann et al.
2016/0113709 A1 4/2016 Maor
2016/0183877 A1 6/2016 Williams et al.
2016/0228023 A1 8/2016 Govari
2016/0228062 A1 8/2016 Altmann et al.
2016/0278853 A1 9/2016 Ogle et al.
2016/0302858 A1 10/2016 Bencini
2016/0324573 A1 11/2016 Mickelson et al.
2016/0338770 A1 11/2016 Bar-Tal et al.
2017/0027638 A1 2/2017 Solis
2017/0035496 A1 2/2017 Nagale et al.
2017/0065227 A1 3/2017 Marrs et al.
2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0143227 A1 5/2017 Marecki et al.
2017/0156790 A1 6/2017 Aujla
2017/0164858 A1 6/2017 Basu
2017/0172442 A1 6/2017 Govari

(56) References Cited

U.S. PATENT DOCUMENTS

2017/0172651 A1 6/2017 Gross et al.
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0265812 A1 9/2017 Williams et al.
2017/0281031 A1 10/2017 Houben et al.
2017/0281268 A1 10/2017 Tran et al.
2017/0296125 A1 10/2017 Altmann et al.
2017/0296251 A1 10/2017 Wu et al.
2017/0319140 A1 11/2017 Wu et al.
2017/0347959 A1 12/2017 Guta et al.
2017/0354338 A1 12/2017 Levin et al.
2017/0354339 A1 12/2017 Zeidan et al.
2017/0354364 A1 12/2017 Bar-Tal et al.
2018/0000540 A1 1/2018 Ogle et al.
2018/0008203 A1 1/2018 Iyun et al.
2018/0028084 A1 2/2018 Williams et al.
2018/0049803 A1 2/2018 Solis
2018/0085064 A1 3/2018 Auerbach et al.
2018/0116595 A1 5/2018 Ruppersberg
2018/0132749 A1 5/2018 Govari et al.
2018/0137687 A1 5/2018 Katz et al.
2018/0160936 A1 6/2018 Govari et al.
2018/0160978 A1 6/2018 Cohen et al.
2018/0161577 A1 6/2018 Goedeke et al.
2018/0168511 A1 6/2018 Hall et al.
2018/0184982 A1 7/2018 Basu et al.
2018/0192958 A1 7/2018 Wu
2018/0192959 A1 7/2018 Mou et al.
2018/0206792 A1 7/2018 Auerbach et al.
2018/0228439 A1 8/2018 Wu et al.
2018/0235692 A1 8/2018 Efimov et al.
2018/0249959 A1 9/2018 Osypka
2018/0256109 A1 9/2018 Wu et al.
2018/0279954 A1 10/2018 Hayam et al.
2018/0303414 A1 10/2018 Toth et al.
2018/0303546 A1 10/2018 Buysman et al.
2018/0310987 A1 11/2018 Altmann et al.
2018/0311497 A1 11/2018 Viswanathan et al.
2018/0338722 A1 11/2018 Altmann et al.
2018/0344188 A1 12/2018 Govari
2018/0344202 A1 12/2018 Bar-Tal et al.
2018/0344251 A1 12/2018 Harlev et al.
2018/0344393 A1 12/2018 Gruba et al.
2018/0360534 A1 12/2018 Teplitsky et al.
2018/0365355 A1 12/2018 Auerbach et al.
2019/0000540 A1 1/2019 Cohen et al.
2019/0008582 A1 1/2019 Govari et al.
2019/0015007 A1 1/2019 Rottmann et al.
2019/0030328 A1 1/2019 Stewart et al.
2019/0053708 A1 2/2019 Gliner
2019/0059766 A1 2/2019 Houben et al.
2019/0069950 A1 3/2019 Viswanathan et al.
2019/0069954 A1 3/2019 Cohen et al.
2019/0117111 A1 4/2019 Osadchy et al.
2019/0117303 A1 4/2019 Claude et al.
2019/0117315 A1 4/2019 Keyes et al.
2019/0125338 A1 5/2019 Shelton, IV et al.
2019/0125437 A1 5/2019 Govari et al.
2019/0125439 A1 5/2019 Rohl et al.
2019/0133552 A1 5/2019 Shemesh et al.
2019/0142293 A1 5/2019 Solis
2019/0164633 A1 5/2019 Ingel et al.
2019/0167137 A1 6/2019 Bar-Tal et al.
2019/0167140 A1 6/2019 Williams et al.
2019/0188909 A1 6/2019 Yellin et al.
2019/0201664 A1 7/2019 Govari
2019/0209089 A1 7/2019 Baram et al.
2019/0216346 A1 7/2019 Ghodrati et al.
2019/0216347 A1 7/2019 Ghodrati et al.
2019/0231421 A1 8/2019 Viswanathan et al.
2019/0231423 A1 8/2019 Weinkam et al.
2019/0239811 A1 8/2019 Just et al.
2019/0246935 A1 8/2019 Govari et al.
2019/0298442 A1 10/2019 Ogata et al.
2019/0314083 A1 10/2019 Herrera et al.
2019/0328260 A1 10/2019 Zeidan et al.
2019/0336210 A1 11/2019 Beeckler et al.
2019/0343580 A1 11/2019 Nguyen et al.
2019/0350567 A1 11/2019 Cummins et al.
2019/0350647 A1 11/2019 Ramberg et al.
2020/0000518 A1 1/2020 Kiernan et al.
2020/0008705 A1 1/2020 Ziv-Ari et al.
2020/0008869 A1 1/2020 Byrd
2020/0009378 A1 1/2020 Stewart et al.
2020/0015876 A1 1/2020 Chou et al.
2020/0015890 A1 1/2020 To et al.
2020/0022653 A1 1/2020 Moisa
2020/0029845 A1 1/2020 Baram et al.
2020/0046421 A1 2/2020 Govari
2020/0046423 A1 2/2020 Viswanathan et al.
2020/0060569 A1 2/2020 Tegg
2020/0077959 A1 3/2020 Altmann et al.
2020/0093539 A1 3/2020 Long et al.
2020/0129089 A1 4/2020 Gliner et al.
2020/0129125 A1 4/2020 Govari et al.
2020/0129128 A1 4/2020 Gliner et al.
2020/0179650 A1 6/2020 Beeckler et al.
2020/0196896 A1 6/2020 Solis
2020/0197082 A1 6/2020 Daniel et al.
2020/0205689 A1 7/2020 Squires et al.
2020/0205690 A1 7/2020 Williams et al.
2020/0205737 A1* 7/2020 Beeckler .............. A61B 5/6853
2020/0205876 A1 7/2020 Govari
2020/0205892 A1 7/2020 Viswanathan et al.
2020/0206461 A1 7/2020 Govari et al.
2020/0206498 A1 7/2020 Arora et al.
2020/0289197 A1 9/2020 Viswanathan et al.
2020/0297234 A1 9/2020 Houben et al.
2020/0297281 A1 9/2020 Basu et al.
2020/0305726 A1 10/2020 Salvestro et al.
2020/0305946 A1 10/2020 DeSimone et al.
2020/0375657 A1 12/2020 Olson et al.
2020/0397328 A1 12/2020 Altmann et al.
2020/0398048 A1 12/2020 Krimsky et al.
2021/0015549 A1 1/2021 Haghighi-Mood et al.
2021/0022684 A1 1/2021 Govari et al.
2021/0045805 A1 2/2021 Govari et al.
2021/0059549 A1 3/2021 Urman et al.
2021/0059550 A1 3/2021 Urman et al.
2021/0059608 A1 3/2021 Beeckler et al.
2021/0059743 A1 3/2021 Govari
2021/0059747 A1 3/2021 Krans et al.
2021/0077180 A1 3/2021 Govari et al.
2021/0077184 A1 3/2021 Basu et al.
2021/0082157 A1 3/2021 Rosenberg et al.
2021/0085200 A1 3/2021 Auerbach et al.
2021/0085204 A1 3/2021 Auerbach et al.
2021/0085215 A1 3/2021 Auerbach et al.
2021/0085387 A1 3/2021 Amit et al.
2021/0093292 A1 4/2021 Baram et al.
2021/0093294 A1 4/2021 Shemesh et al.
2021/0093374 A1 4/2021 Govari et al.
2021/0093376 A1 4/2021 Harlev et al.
2021/0093377 A1 4/2021 Herrera et al.
2021/0100612 A1 4/2021 Baron et al.
2021/0113822 A1 4/2021 Beeckler et al.
2021/0127999 A1 5/2021 Govari et al.
2021/0128010 A1 5/2021 Govari et al.
2021/0133516 A1 5/2021 Govari et al.
2021/0145282 A1 5/2021 Bar-Tal et al.
2021/0161582 A1 6/2021 Byrd et al.
2021/0161592 A1 6/2021 Altmann et al.
2021/0162210 A1 6/2021 Altmann et al.
2021/0169421 A1 6/2021 Govari
2021/0169550 A1 6/2021 Govari et al.
2021/0169567 A1 6/2021 Govari et al.
2021/0169568 A1 6/2021 Govari et al.
2021/0177294 A1 6/2021 Gliner et al.
2021/0177356 A1 6/2021 Gliner et al.
2021/0177503 A1 6/2021 Altmann et al.
2021/0178166 A1 6/2021 Govari et al.
2021/0186363 A1 6/2021 Gliner et al.

(56) References Cited

U.S. PATENT DOCUMENTS

| | | | |
|---|---|---|---|
| 2021/0186604 | A1 | 6/2021 | Altmann et al. |
| 2021/0187241 | A1 | 6/2021 | Govari et al. |
| 2021/0187254 | A1 | 6/2021 | Beeckler et al. |
| 2021/0196372 | A1 | 7/2021 | Altmann et al. |
| 2021/0196394 | A1 | 7/2021 | Govari et al. |
| 2021/0212591 | A1 | 7/2021 | Govari et al. |
| 2021/0219904 | A1 | 7/2021 | Yarnitsky et al. |
| 2021/0236815 | A1 | 8/2021 | Waldstreicher et al. |
| 2021/0278936 | A1 | 9/2021 | Katz et al. |
| 2021/0282659 | A1 | 9/2021 | Govari et al. |
| 2021/0307815 | A1 | 10/2021 | Govari et al. |
| 2021/0308424 | A1 | 10/2021 | Beeckler et al. |
| 2021/0338319 | A1 | 11/2021 | Govari et al. |
| 2021/0369339 | A1 | 12/2021 | Salazar et al. |
| 2022/0071695 | A1 | 3/2022 | Beeckler et al. |
| 2022/0071696 | A1 | 3/2022 | Beeckler et al. |
| 2022/0110679 | A1 | 4/2022 | Wang et al. |
| 2022/0304745 | A1 | 9/2022 | Olson |
| 2022/0387051 | A1 | 12/2022 | Girdhar |
| 2023/0000550 | A1 | 1/2023 | Nedved et al. |
| 2023/0130692 | A1 | 4/2023 | Wang et al. |
| 2023/0225790 | A1 | 7/2023 | Okarski |
| 2023/0346455 | A1 | 11/2023 | Beeckler et al. |
| 2023/0346459 | A1 | 11/2023 | Beeckler et al. |
| 2023/0346462 | A1 | 11/2023 | Beeckler et al. |
| 2023/0346464 | A1 | 11/2023 | Beeckler et al. |
| 2024/0216045 | A1 | 7/2024 | Keyes |
| 2025/0057589 | A1 | 2/2025 | Sandquist et al. |

FOREIGN PATENT DOCUMENTS

| | | | |
|---|---|---|---|
| CN | 111248996 | A | 6/2020 |
| EP | 0668740 | A1 | 8/1995 |
| EP | 0644738 | B1 | 3/2000 |
| EP | 0727183 | B1 | 11/2002 |
| EP | 0727184 | B1 | 12/2002 |
| EP | 2201905 | A1 | 6/2010 |
| EP | 2783651 | A1 | 10/2014 |
| EP | 2699151 | B1 | 11/2015 |
| EP | 2699152 | B1 | 11/2015 |
| EP | 2699153 | B1 | 12/2015 |
| EP | 2498706 | B1 | 4/2016 |
| EP | 2578173 | B1 | 6/2017 |
| EP | 3181082 | A1 | 6/2017 |
| EP | 3238645 | A1 | 11/2017 |
| EP | 2884931 | B1 | 1/2018 |
| EP | 3315086 | A1 | 5/2018 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3791816 | A2 | 3/2021 |
| EP | 3972510 | A1 | 3/2022 |
| EP | 4115834 | A1 | 1/2023 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020194216 | A1 | 10/2020 |
| WO | 2020206328 | A1 | 10/2020 |
| WO | 2021126980 | A1 | 6/2021 |
| WO | 2022001908 | A1 | 1/2022 |

OTHER PUBLICATIONS

Extended European Search Report dated Feb. 2, 2023, from Corresponding European Application No. 22194819.3, 8 pages.

Extended European Search Report and Opinion dated Jun. 1, 2023, from corresponding European Application No. 23152493.5.

Extended European Search Report and Opinion dated Jun. 7, 2023, from corresponding European Application No. 23152399.4.

Extended European Search Report and Opinion dated Jun. 12, 2023, from corresponding European Application No. 23152448.9.

Extended European Search Report dated Jun. 13, 2023, from Corresponding European Application No. 23152458.8, 12 pages.

Extended European Search Report and Opinion dated Sep. 6, 2023, from corresponding European Application No. 23152472.9.

Extended European Search Report & Search Opinion dated Sep. 19, 2023, from corresponding European Application No. 23170233.3.

Extended European Search Report & Search Opinion dated Sep. 19, 2023, from corresponding European Application No. 23170325.7.

Extended European Search Report & Search Opinion dated Sep. 21, 2023, from corresponding European Application No. 23170230.9.

Extended European Search Report & Search Opinion dated Sep. 21, 2023, from corresponding European Application No. 23170409.9.

Extended European Search Report & Search Opinion dated Jan. 2, 2024, from corresponding European Application No. 23170297.8.

* cited by examiner

ELECTRODE ASSEMBLIES OF A BASKET CATHETER HAVING MECHANICAL RETAINERS AND METHODS OF THE SAME

CROSS REFERENCE TO RELATED APPLICATIONS

This application claims the benefit of priority under 35 U.S.C. § 119 to prior filed U.S. Provisional Patent Application No. 63/301,146 filed on Jan. 20, 2022, the entire contents of which is hereby incorporated by reference as if set forth in full herein.

FIELD

The present invention relates generally to medical devices, and in particular catheters with electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain drawbacks, such as heightened risk of thermal cell injury which can lead to tissue charring, burning, steam pop, phrenic nerve palsy, pulmonary vein stenosis, and esophageal fistula. Cryoablation is an alternative approach to RF ablation that generally reduces thermal risks associated with RF ablation. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated by reference in their entirety into this application as if set forth in full and attached in the appendix to priority application U.S. 63/301,146.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Due to the small size of the spines and the electrodes, however, soldering, welding, or adhering the electrodes to the spines can be a difficult task, increasing the manufacturing time and cost and the chances that the electrode fails due to an improper bond or misalignment. What is needed, therefore, are systems and methods of attaching an electrode to a spine of a basket assembly without the need for soldering, welding, or using adhesive.

SUMMARY

There is provided, in accordance with an embodiment of the present invention, a medical probe, including an expandable basket assembly coupled to a distal end of a tubular shaft. The expandable basket assembly can include at least one spine and a plurality of electrode assemblies. The electrode assemblies can each include a first insulating portion and a second insulating portion that can electrically insulate the electrode from the spine. The electrode, the first insulating portion, and the second insulating portion can be interlocked onto a spine to prevent the electrode from sliding proximally or distally along a length of the spine. In this way, the presently disclosed technology can be used to secure the electrodes to the spines without requiring solder, weld, or adhesives.

The disclosed technology includes a medical probe including a tubular shaft having a proximal end and a distal end. The tubular shaft can extend along a longitudinal axis. The medical probe can further include an expandable basket assembly coupled to the distal end of the tubular shaft.

The expandable basket assembly can include at least one spine extending along the longitudinal axis and configured to bow radially outward from the longitudinal axis when the expandable basket assembly is transitioned from a collapsed form to an expanded form. The expandable basket assembly can include a plurality of electrode assemblies. Each electrode assembly of the plurality of electrode assemblies can be attached to the at least one spine. Each electrode assembly can include an electrode, a first electrically insulating portion electrically isolating the electrode from the respective spine, and a second electrically insulating portion electrically isolating the electrode from the spine. The electrode, the first electrically insulating portion, and the second electrically insulating portion can be interlocked onto the spine such that the plurality of electrode assemblies are prevented from sliding proximally or distally along a length of the spine.

The spine can include a retainer ring onto which a respective electrode assembly of the plurality of electrode assemblies is interlocked. The electrode can include a protrusion that is configured to interlock with the second electrically insulating portion. The protrusion can extend through the retainer ring, thereby preventing the electrode assembly from sliding along the length of the spine. The protrusion can include a swage fitting.

The first electrically insulating portion can include a first washer and the second electrically insulating portion can include a second washer. The first washer and the second washer can be configured to prevent the electrode from contacting the spine and to electrically isolate the electrode from the spine. The second washer can include a lip that is configured to extend inwardly into the retainer ring to prevent the electrode from contacting the spine.

The first electrically insulating portion can be a first housing portion and the second electrically insulating portion can be a second housing portion. The first housing portion and the second housing portion can be configured to interlock to secure the electrode to the spine. The second housing portion can include a male connector and the first housing portion can include a female connector configured receive the male connector and facilitate the first housing portion to interlock with the second housing portion. Alternatively, the first housing portion can include a male connector and the second housing portion can include a female connector configured receive the male connector and facilitate the first housing portion to interlock with the second housing portion.

The first housing portion can include a rim that is configured to receive the electrode. The electrode can further include a base portion that is configured to retain the electrode in the rim of the first housing portion. The base portion can include an outer perimeter length that is greater than an inner perimeter length of the rim.

The electrode can be electrically connected to a wire of the medical probe. At least a portion of the wire can include an electrically conductive core material comprising a first electrical conductivity and an electrically conductive cover material comprising a second electrical conductivity less than the first electrical conductivity. The electrically conductive cover material can circumscribe the electrically conductive core material and an insulative jacket can circumscribe the electrically conductive cover material. At least a portion of the wire can include a plurality of strands and an insulative jacket circumscribing the plurality of the strands. Each strand of the plurality of strands respectively can include an electrically conductive core material comprising a first electrical conductivity and an electrically conductive cover material comprising a second electrical conductivity less than the first electrical conductivity. The electrically conductive cover material can circumscribe the electrically conductive core material.

The at least one spine of the medical probe can include nitinol, cobalt chromium, or other suitable material.

The plurality of electrodes can be configured to deliver electrical pulses for irreversible electroporation, the pulses having a peak voltage of at least 900 volts (V).

The at least one spine can be configured to form an approximately spherically-shaped basket assembly or an approximately oblate-spheroid basket assembly when in the expanded form.

The medical probe can further include irrigation openings that can be configured to deliver an irrigation fluid to the plurality of electrodes.

The medical probe can further include an electrically insulative jacket each disposed between the at least one spine and a respective electrode of the plurality of electrodes, thereby electrically isolating the plurality of electrodes from the plurality of spines. Each of the electrically insulative jackets of the plurality of electrically insulative jackets can include a first lumen and a second lumen. The first lumen can be configured to receive a first wire and the second lumen can be configured to receive the respective spine. Furthermore, a cross-sectional shape of each electrically insulative jacket can include a substantially trapezoidal shape.

The disclosed technology can include a method of constructing a medical probe. The method can include aligning an electrode, a first insulated portion, and a second insulated portion. The method can include placing a spine of a basket catheter between the first insulated portion and the second insulated portion and interlocking the electrode, the first insulated portion, and the second insulated portion together to secure the electrode to the spine. The electrode, the first insulated portion, and the second insulated portion can be secured to the spine such that the first insulated portion and the second insulated portion electrically isolate the electrode from the spine and such that the electrode, the first insulated portion, and the second insulated portion are prevented from sliding proximally or distally along a length of the respective spine.

Interlocking the electrode, the first insulated portion, and the second insulated portion together can include interlocking a portion of at least one of the electrodes, the first insulated portion, and the second insulated portion through an aperture of a retainer ring of the spine. The method can include aligning the electrode, the first insulated portion, and the second insulated portion with the retainer ring.

Interlocking the electrode, the first insulated portion, and the second insulated portion together can include interlocking a protrusion of the electrode with the second insulated portion. The method can include forming a swage fitting on the protrusion to cause the electrode to interlock with the second insulated portion. Interlocking the electrode, the first insulated portion, and the second insulated portion together can include extending the protrusion through the retainer ring thereby preventing the electrode from sliding proximally or distally along the length of the spine.

The first insulated portion can include a first insulated washer and the second insulated portion can include a second insulated washer. The method can include positioning the first insulated washer and the second insulated washer so that the electrode is electrically isolated from the spine.

Interlocking the electrode, the first insulated portion, and the second insulated portion together can include extending a lip of the second insulated washer inwardly into the retainer ring thereby preventing the electrode from contacting the spine.

The first insulated portion can include a first insulated housing portion and the second insulated portion can include a second insulated housing portion. Interlocking the electrode, the first insulated portion, and the second insulated portion together can include interlocking the first insulated housing portion and the second insulated housing portion to thereby secure the electrode to the spine.

The second insulated housing portion can include a male connector and the first insulated housing portion can include a female connector that is configured receive the male connector and facilitate the first insulated housing portion to interlock with the second insulated housing portion.

The first insulated housing portion can include a rim that is configured to receive the electrode. Interlocking the electrode, the first insulated portion, and the second insulated portion together can include retaining a base portion of the electrode in the rim. The base portion can include an outer perimeter length that is greater than an inner perimeter length of the rim.

The method can include electrically connecting the electrode to a wire of the medical probe. At least a portion of the wire can include an electrically conductive core material comprising a first electrical conductivity and an electrically conductive cover material comprising a second electrical conductivity less than the first electrical conductivity. The electrically conductive cover material can circumscribe the electrically conductive core material and an insulative jacket can circumscribe the electrically conductive cover material. At least a portion of the wire can include a plurality of strands and an insulative jacket circumscribing the plurality of the strands. Each strand of the plurality of strands respectively can include an electrically conductive core material comprising a first electrical conductivity and an electrically conductive cover material comprising a second electrical conductivity less than the first electrical conductivity. The electrically conductive cover material can circumscribe the electrically conductive core material.

Each spine of the plurality of spines of the medical probe can include nitinol, cobalt chromium, or other suitable material.

The plurality of electrodes can be configured to deliver electrical pulses for irreversible electroporation, the pulses having a peak voltage of at least 900 volts (V).

The plurality of spines can be configured to form an approximately spherically-shaped basket assembly or an approximately oblate-spheroid basket assembly when in the expanded form.

The medical probe can further include irrigation openings that can be configured to deliver an irrigation fluid to the plurality of electrodes.

The medical probe can further include a plurality of electrically insulative jackets each disposed between a respective spine of the plurality of spines and a respective electrode of the plurality of electrodes, thereby electrically isolating the plurality of electrodes from the plurality of spines. Each of the electrically insulative jackets of the plurality of electrically insulative jackets can include a first lumen and a second lumen. The first lumen can be configured to receive a first wire and the second lumen can be configured to receive the respective spine. Furthermore, a cross-sectional shape of each electrically insulative jacket can include a substantially trapezoidal shape.

DETAILED DESCRIPTION

Figure 1:
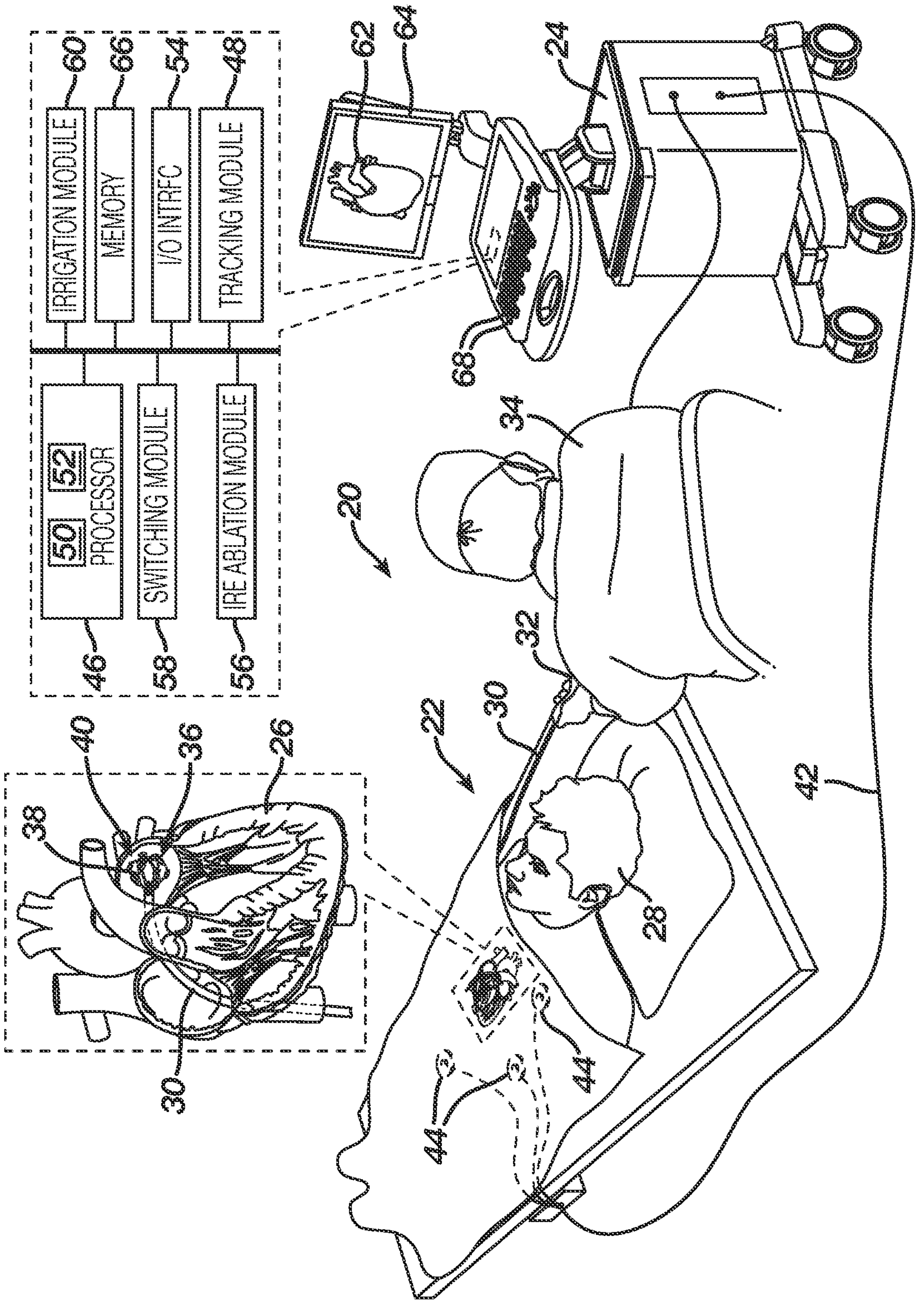
FIG. 1 is a schematic pictorial illustration of a medical system comprising a medical probe whose distal end comprises a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 110%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator or physician whereas "distal" indicates a location further away to the operator or physician.

As discussed herein, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal having a positive-voltage phase pulse (referred to herein as "positive phase") and a negative-voltage phase pulse (referred to herein as "negative phase"). "Monophasic pulse" refers to an electrical signal having only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape having an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, method or uses and devices which utilize end effectors having electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by apoptosis. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated by reference in its entirety into this application as if set forth in full and attached in the appendix to priority application U.S. 63/301,146.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated by reference into this application as if set forth in full and attached in the appendix to priority application U.S. 63/301,146.

To deliver pulsed field ablation (PFA) in an IRE (irreversible electroporation) procedure, electrodes should contact the tissue being ablated with a sufficiently large surface area. As described hereinbelow, the medical probe includes a flexible insertion tube having proximal and distal ends, and a basket assembly at the distal end of the flexible insertion tube. The basket assembly includes at least one spine and a plurality of electrode assemblies. Each electrode assembly can be configured to interlock with the spine to prevent the spine from sliding proximally or distally along the length of the spine.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the insertion tube. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 affixed to distal end 36. Basket assembly 38 can include a plurality of electrodes 40 affixed to a plurality of spines, as described in the description referencing FIGS. 2A and 2B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 engages cardiac tissue, the medical professional 34 can activate the medical probe 22 such that electrical pulses are delivered by the electrodes 40 to perform the IRE ablation.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses having peak power in the range of tens of kilowatts. In some examples, the electrodes 40 are configured to deliver electrical pulses having a peak voltage of at least 900 volts (V) and in some instances 1100V or higher. The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

Where irrigation is desired, system 20 supplies irrigation fluid (e.g., a saline solution) to distal end 36 and to the electrodes 40 via a channel (not shown) in insertion tube 30. Control console 24 includes an irrigation module 60 to monitor and control irrigation parameters, such as the pressure and the temperature of the irrigation fluid.

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

Figure 2A:
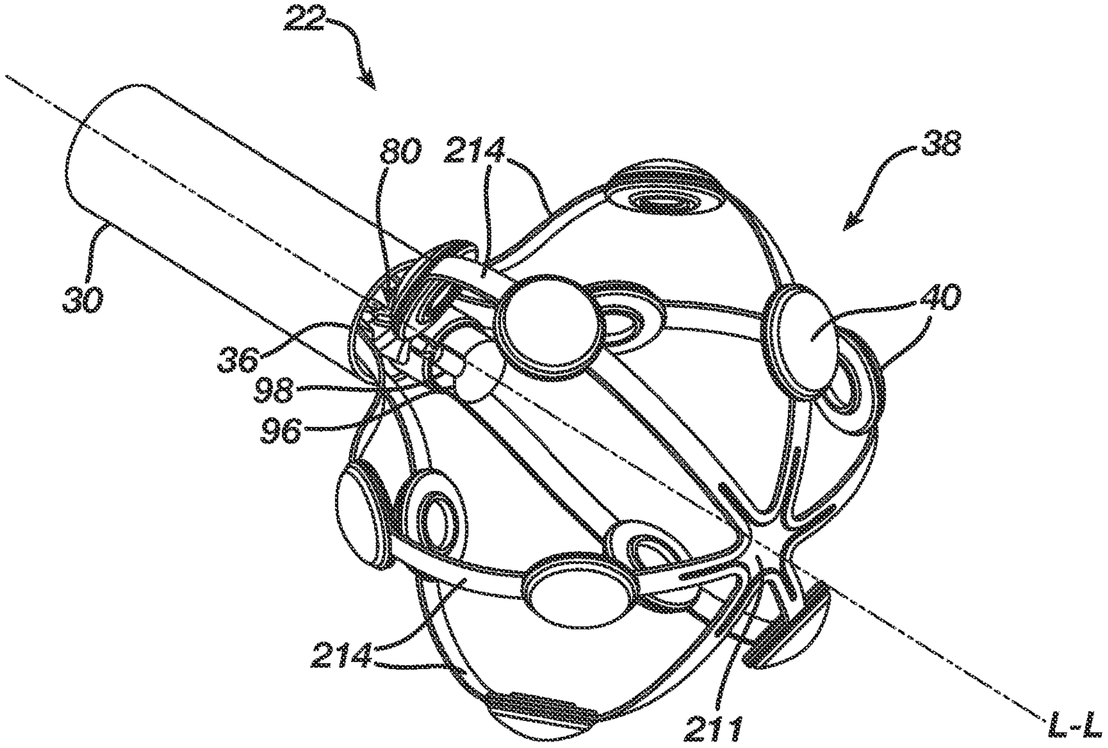
FIG. 2A is a schematic pictorial illustration showing a perspective view of a medical probe in an expanded form, in accordance with an embodiment of the present invention.
Figure 2B:
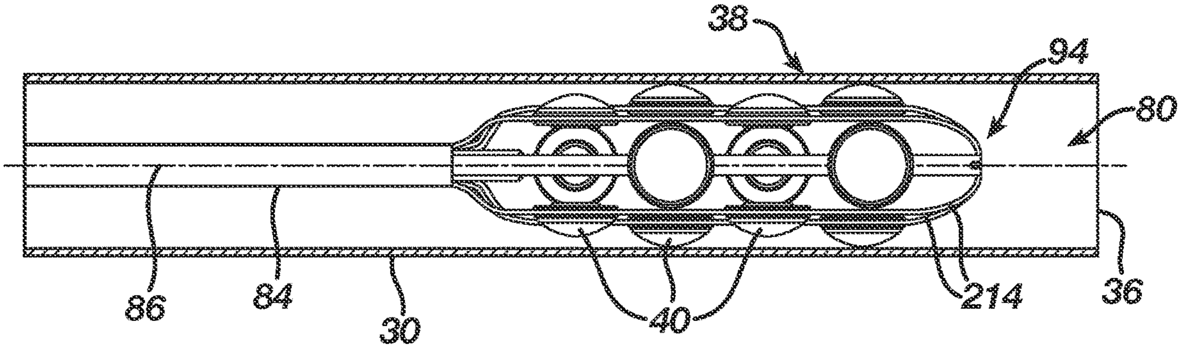
FIG. 2B is a schematic pictorial illustration showing a side view of a medical probe in a collapsed form, in accordance with the disclosed technology.

FIG. 2A is a schematic pictorial illustration showing a perspective view of a medical probe 22 with a basket assembly 38 in an expanded form when unconstrained, such as by being advanced out of an insertion tube lumen 80 at a distal end 36 of an insertion tube 3. FIG. 2B shows the basket assembly in a collapsed form within insertion tube 30. In the expanded form (FIG. 2A), the spines 214 bow radially outwardly and in the collapsed form (FIG. 2B) the spines are arranged generally along a longitudinal axis 86 of insertion tube 30.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing the basket assembly 38 to exit the insertion tube and transition to the expanded form. Spines 214 may have elliptical (e.g., circular) or rectangular (that may appear to be flat) cross-sections, and include a flexible, resilient material (e.g., a shape-memory alloy such as nickel-titanium (also known as Nitinol), cobalt chromium, or any other suitable material).

In embodiments described herein, electrodes 40 can be configured to deliver ablation energy (RF and/or IRE) to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the electrode 40 faces outwardly from the basket assembly 39 such that the electrodes 40 deliver a greater amount of electrical energy outwardly away from the basket assembly 38 (i.e., toward the heart 26 tissue) than inwardly toward the basket assembly 38.

Examples of materials ideally suited for forming electrodes 40 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Basket assembly 38 has a distal end 94 and includes a stem 96 that extends longitudinally from a distal end 36 of tubular shaft 84 towards distal end 94 of basket assembly 38. As described supra, control console 24 includes irrigation module 60 that delivers irrigation fluid to distal end 36. Stem 96 includes multiple irrigation openings 98, wherein each given irrigation opening 98 can be angled to spray or otherwise disperse of the irrigation fluid to either a given electrode 40 or to tissue in heart 26.

Since electrodes 40 do not include irrigation openings that deliver irrigation fluid, the configuration described hereinabove enables heat to be transferred from the tissue (i.e., during an ablation procedure) to the portion of the electrodes on the inner side of the spines 214, and the electrodes 40 can be cooled by aiming the irrigation fluid, via irrigation openings 98, at the portion of the electrodes 40 on the inner side of the spines 214.

Figure 3A:
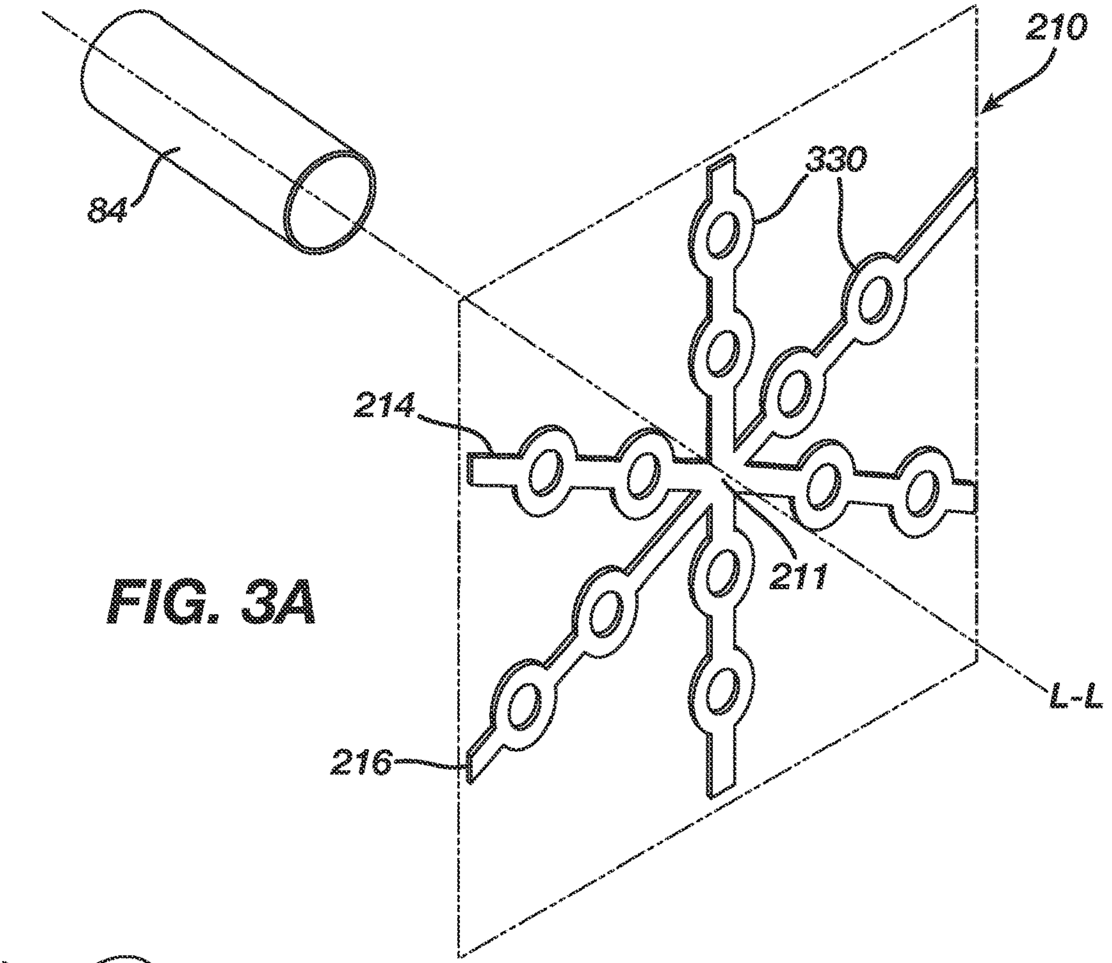
FIGS. 3A and 3B are schematic pictorial illustrations showing exploded views of a tubular shaft and spines of the basket assembly to illustrate how the spines can be assembled together with the tubular shaft, in accordance with an embodiment of the present invention.
Figure 3B:
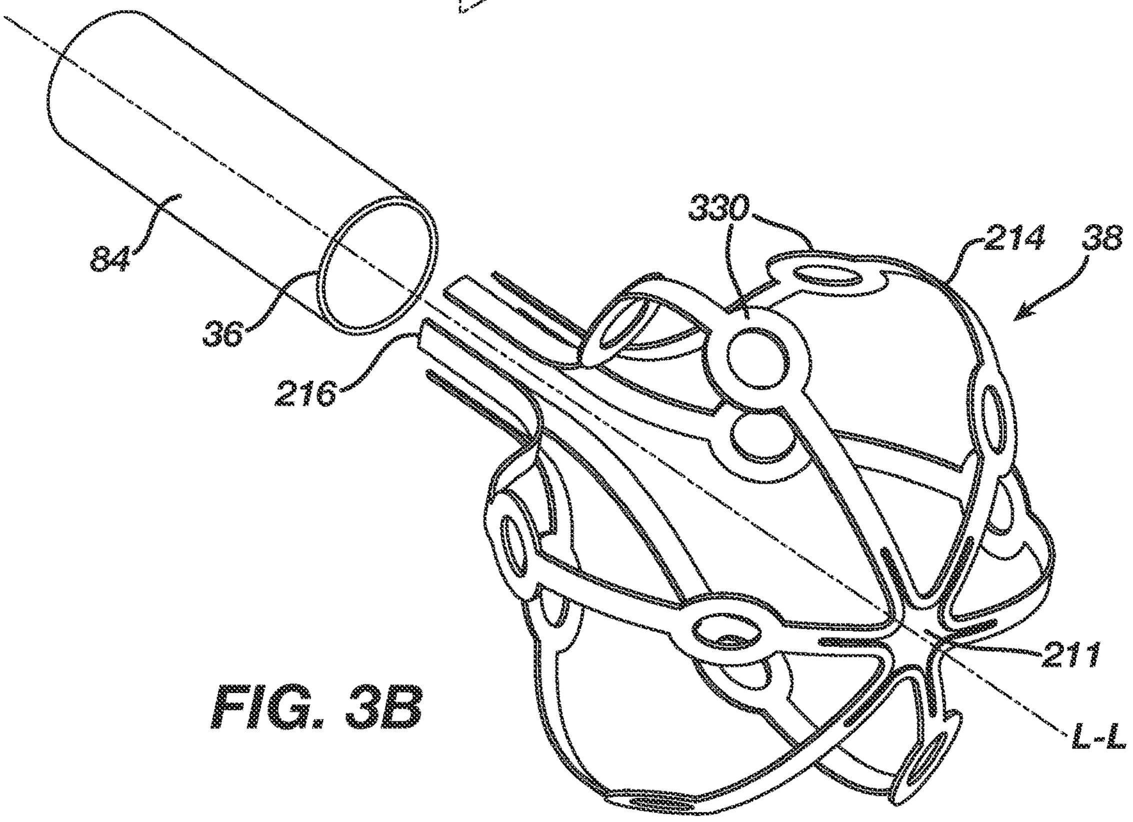

FIGS. 3A and 3B are schematic pictorial illustrations showing exploded views of a tubular shaft 84 and spines 214 of the basket assembly to provide one example of how the spines 214 can be assembled together with the tubular shaft 84, in accordance with an embodiment of the present invention. As shown in FIG. 3A, the spines 214 can be formed from a single sheet of planar material to form a generally star shape. In other words, the spines 214 can be formed from the single sheet of planar material such that the spines 214 converge toward a central intersection 211. The intersection 211 can be a solid piece of material (as shown in FIG. 3A) or include one or more apertures (as shown in FIG. 3B).

The spines 214 can be folded or otherwise bent such that a proximal end 216 of the spines 214 can be inserted into the distal end 85 of the tubular shaft 84 as shown in FIG. 3B. Although not shown in FIGS. 3A and 3B, it will be appreciated that the electrodes 40 can be attached to the spines 214 before the spines are inserted into the tubular shaft 84 to form the basket assembly 38. As stated previously, the spines 214 can include a flexible, resilient material (e.g., a shape-memory alloy such as nickel-titanium, also known as Nitinol) that can enable the basket assembly 38 to transition from its collapsed form (as shown in FIG. 2B) to its expanded form (as shown in FIG. 2A) when the basket assembly 38 is deployed from insertion tube 30. As will become apparent throughout this disclosure, the spine 214 can be electrically isolated from the electrode 40 to prevent arcing from the electrode 40 to the spine 214.

As will be appreciated by one skilled in the art with the benefit of this disclosure, the basket assembly 38 shown in FIGS. 2A-3B having spines 214 formed from a single sheet of planar material and converging at a central intersection is offered merely for illustrative purposes and the disclosed technology can be applicable to other configurations of basket assemblies 38. For example, the disclosed technology can be applicable to basket assemblies 38 formed from a single spine 214 or multiple spines 214 with each spine 214 being attached at both ends. In other examples, the basket assembly 38 can include a central hub connecting the multiple spines 214 together at a distal end 94 of the basket assembly 38. In yet other examples, the basket assembly 38 can include a single spine 214 configured to form a spiral, multiple spines 214 configured to form a spiral, multiple spines 214 configured to form a tripod or multiple tripods, or any other shape of basket assembly 38. As well, the spine assembly 210 can be formed by laser cutting a cylindrical hollow stock material whereby the laser is mounted for rotation about the longitudinal axis (and translation thereto) of the cylindrical stock while cutting through the cylindrical stock. Thus, although FIGS. 2A-3B illustrate a specific configuration of basket assembly 38, the disclosed technology should not be construed as so limited.

Turning now to FIGS. 4A-10D, various examples of electrode assemblies 300, 800 will be described. As will become apparent throughout this disclosure, the electrode assemblies 300, 800 can be configured to attach the electrodes 340, 840 to the spines 214 and prevent the electrodes 340, 840 from sliding proximally or distally along the length of the spine 214. Generally speaking, the electrode assemblies 300, 800 can include an electrode 340, 840, a first electrically insulating portion (i.e., a first washer 350 or a first insulated housing portion 870, as described herein), and a second electrically insulating portion (i.e., a second washer 350 or a second insulated housing portion 880, as described herein). The first insulating portion and the second insulating portion can electrically isolate the electrode 340, 840 from the spine 214. As will be appreciated, although the electrode assemblies 300, 800 are described as having a first and a second electrically insulating portion, one of skill in the art will appreciate that insulative coatings can be used in addition to, or in place of, the insulating portions described herein.

The electrode assemblies 300, 800 are preferably asymmetrical with respect to a plane of the spine such that the electrode 340 presents an electrically conductive surface area facing outwardly from a periphery of the basket of the catheter and an insulating surface faces inwardly from the periphery of the basket. Furthermore, as will be appreciated by one of skill in the art, the electrodes 340, 840 can be the same as, or in place of, the electrode 40 previously described herein. That is, the electrode assemblies 300, 800 are examples of the present disclosure that can be used to attach the electrodes 340, 840 to the spine 214 to facilitate the electrodes 340, 840 performing the same or a similar function as the electrodes 40 described herein (e.g., delivering IRE ablation energy to cardiac tissue). One of skill in the art will appreciate that the electrode assemblies 300, 800 described herein are offered for illustrative purposes and that other electrode assemblies having similar features can reasonably be construed as falling within the scope of this disclosure. Thus, the present disclosure should not be construed as limited to the particular electrode assemblies 300, 800 shown in FIGS. 4A-10D and described herein.

Figure 4A:
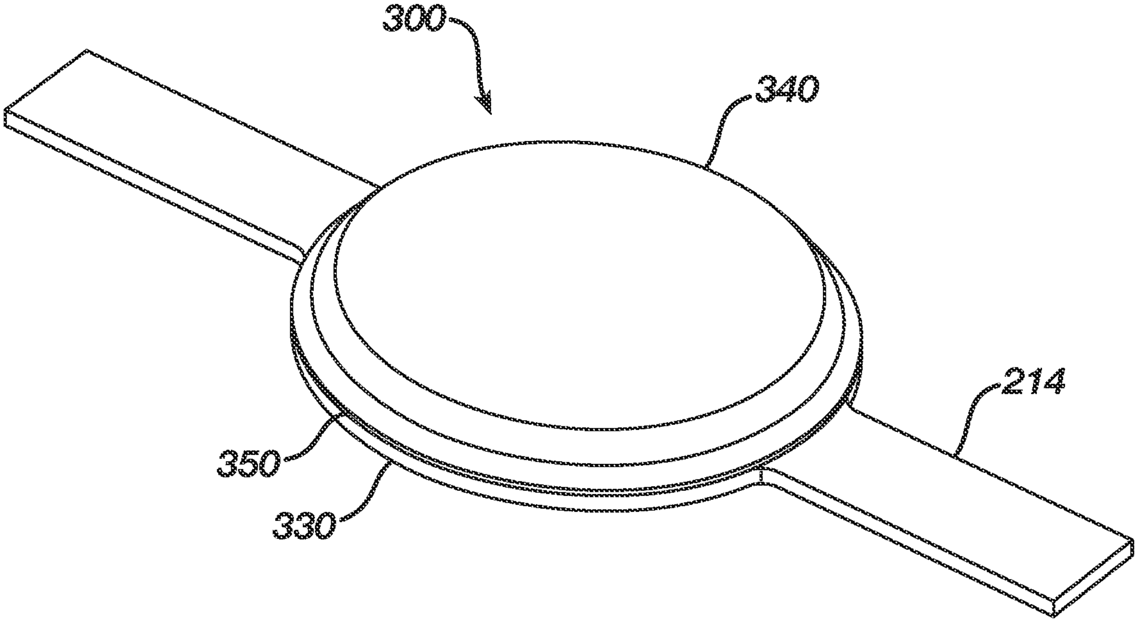
FIGS. 4A and 4B are schematic pictorial illustrations showing perspective views of an electrode attached to a spine, in accordance with an embodiment of the present invention.
Figure 4B:
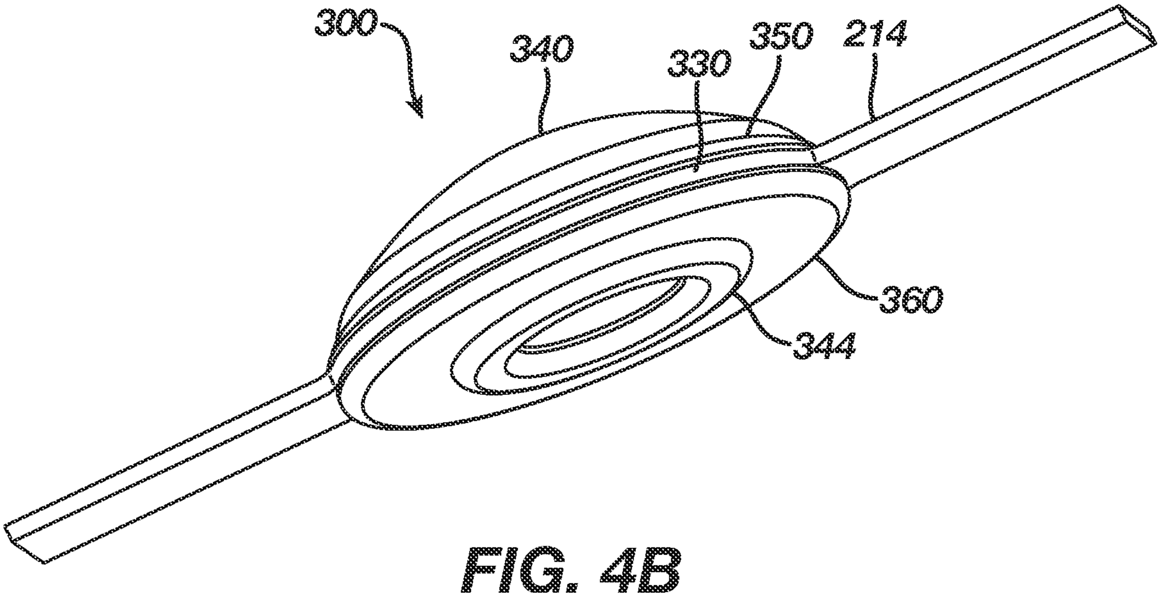

FIGS. 4A and 4B are schematic pictorial illustrations showing perspective views of an electrode assembly 300 attached to a spine 214, in accordance with an embodiment of the present invention. The electrode assembly 300 can include an electrode 340, a first washer 350, and a second washer 360. The electrode 340 can include electrically conductive material as described in relation to the electrode 40 (e.g., gold, platinum, and palladium (and their respective alloys)). The first washer 350 and the second washer 360 can be made from a biocompatible, electrically insulative material such as polyetherimide (Ultem), polyimide, polyetheretherketon (PEEK), polytetraflouroethylene (PTFE), flourinated ethylene propylene (FEP), etc. Furthermore, the first washer 350 and the second washer 360 can include filler materials such as PTFE (for insulation), boron nitride (for insulation), diamond (for thermal conductivity), etc. In this way, the first washer 350 and the second washer 360 can be configured to electrically isolate the electrode 340 from the spine 214 to prevent or reduce arcing between the electrode 340 and the spine 214.

The electrode 340, the first washer 350, and the second washer 360 can be configured to interlock with each other to form the electrode assembly 300. Furthermore, as will be described in greater detail herein, the electrode 340, the first washer 350, and the second washer 360 can be configured to interlock with a spine 214 to prevent the electrode assembly 300 from sliding proximally or distally along the length of the spine 214. To help prevent the electrode assembly 300 from sliding proximally or distally along the length of the spine 214, the spine 214 can include a retainer ring 330 that can be a ring formed in the spine 214 comprising an aperture 332 through which portions of the electrode assembly 300 can pass. The retainer ring 330 may be better observed in, and is described in relation to, FIGS. 6 and 7A.

Figure 5:
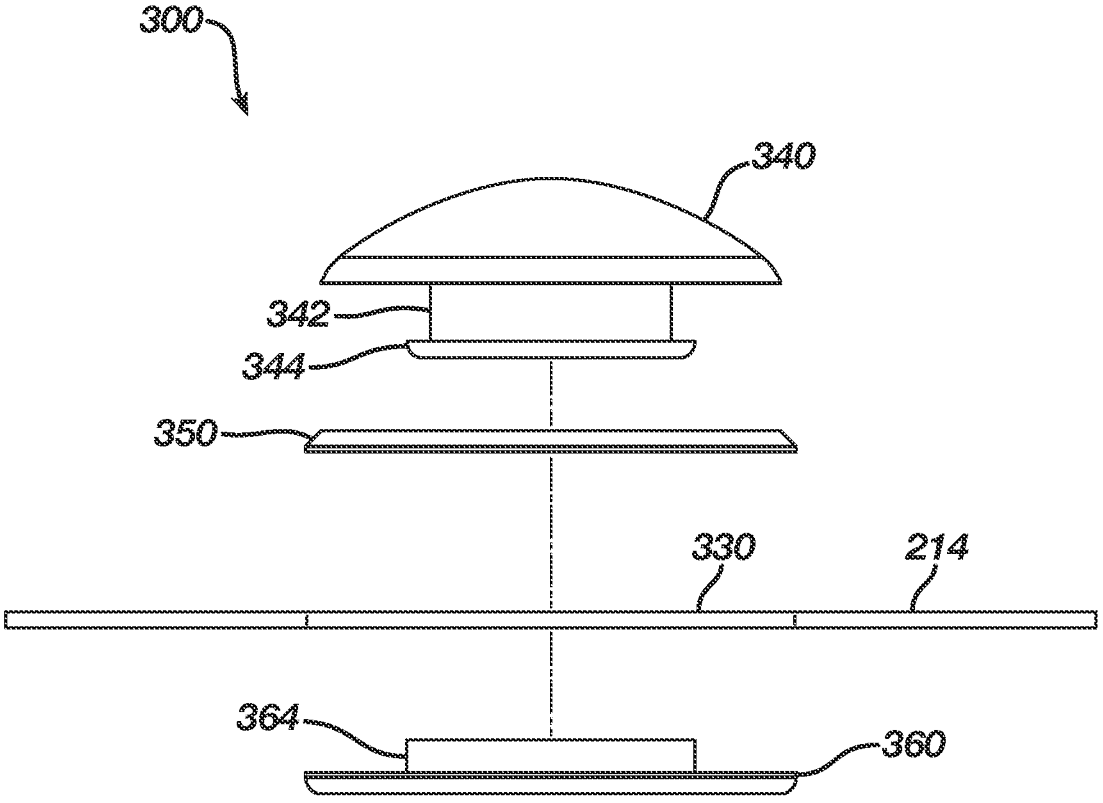
FIG. 5 is a schematic pictorial illustration showing a side exploded view of an electrode assembly and a spine, in accordance with an embodiment of the present invention.
Figure 6:
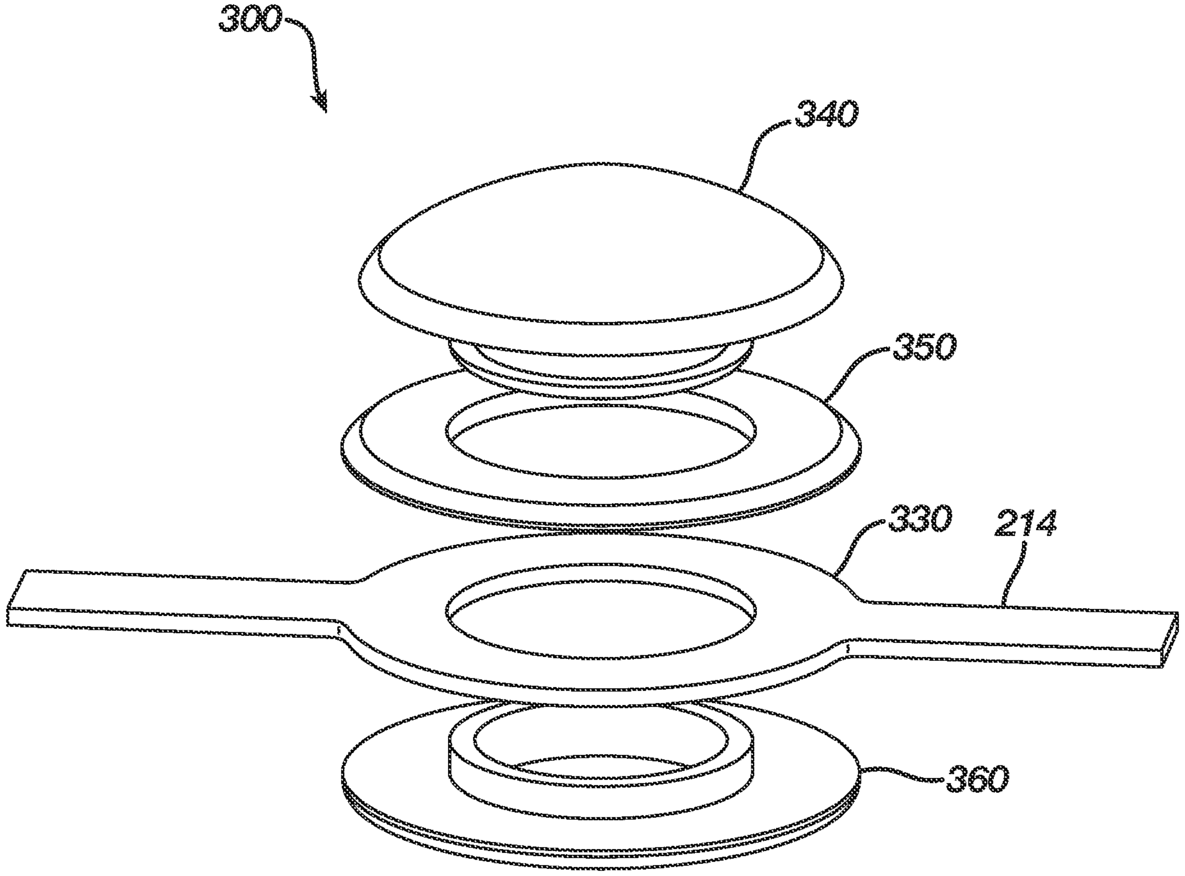
FIG. 6 is a schematic pictorial illustration showing a perspective exploded view of an electrode assembly and a spine, in accordance with an embodiment of the present invention.

FIG. 5 is a schematic pictorial illustration showing a front exploded view of an electrode assembly 300 and a spine 214 while FIG. 6 is a schematic pictorial illustration showing a perspective exploded view of an electrode assembly 300 and a spine 214, in accordance with an embodiment of the present invention. As illustrated in FIGS. 5 and 6, the electrode 340 and the first washer 350 can be positioned on a first side of the spine 214 while the second washer 360 can be positioned on a second side of the spine 214. Thus, when the electrode 340, the first washer 350, and the second washer 360 are pushed together to be attached to the spine 214, the spine 214 can be positioned between portions of the electrode assembly 300. Furthermore, as illustrated in FIG. 6, at least a portion of the electrode 340 can be configured to pass through the aperture 332 of the retainer ring 330 to help secure the electrode assembly 300 to the spine 214. In other words, because at least a portion of the electrode 340 can pass through the retainer ring 330, the electrode assembly 300 can be secured together through the retainer ring 330 such that the electrode assembly 300 is prevented from becoming disengaged with, or sliding along, the spine 214.

The electrode assembly 300 can be secured in place by including a mechanical interference that can prevent the electrode assembly 300 from separating once secured together. For example, the electrode 340 and at least the second washer 360 can be configured to form an interference fit together when pressed together to prevent the electrode 340 from becoming disengaged with the second washer 360. For example, an outer diameter of a protrusion of 342 of the electrode 340 can be slightly larger than the inner diameter of an aperture 362 through the second washer 360 to form an interference fit between the electrode 340 and the second washer 360 when pressed together.

As another example, the electrode 340 can include a swage fitting 344 that can be sized to secure the electrode assembly 300 in place once the electrode 340 is engaged with the second washer 360. The swage fitting 344 can be formed as the electrode 340 is pushed together with the second washer 360 with use of a tool adapted to form a swage fitting. Alternatively, or in addition, the swage fitting 344 can be formed prior to pressing the electrode 340 and the second washer 360 together. For example, the swage fitting 344, the second washer 360, or both, can comprise a resilient material that can deflect as the swage fitting 344 is pushed through an aperture 362 of the second washer 360. The swage fitting 344 can then return (or nearly) to its original configuration after being pushed through the aperture 362 of the second washer 360 such that the electrode assembly 300 is secured in place. In other words, the swage fitting 344 and the aperture 362 of the second washer 360 can both be configured to allow a portion of the electrode 340 to pass through the aperture 362 of the second washer 360 in a first direction but prevent the electrode 340 from passing through the aperture 362 in a second direction and becoming disengaged with the second washer 360 after assembly. As will be appreciated by one of skill in the art, although the electrode assembly 300 is illustrated as having a second washer 360 having an aperture 362 configured to receive at least a portion of an electrode 340 to secure the electrode assembly 300 in place, the disclosed technology is not so limited. As a non-limiting example, the configuration of the electrode assembly 300 may be switched and the electrode 340 may comprise an aperture (or multiple apertures) configured to receive a protrusion of the second washer 360 to secure electrode assembly 300 in place.

Figure 7A:
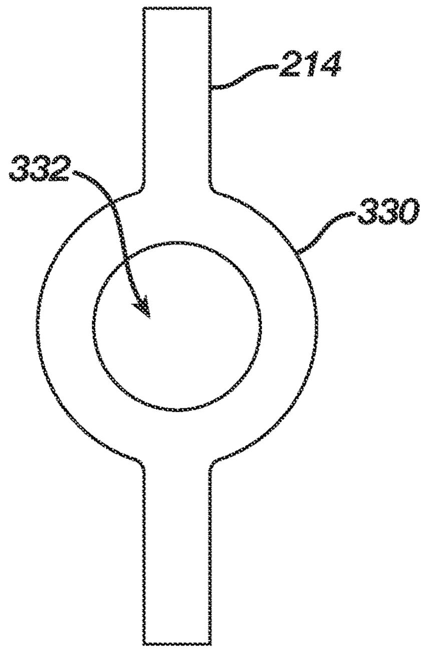
FIG. 7A is a schematic pictorial illustration showing a top view of a spine, in accordance with another embodiment of the present invention.
Figure 7B:
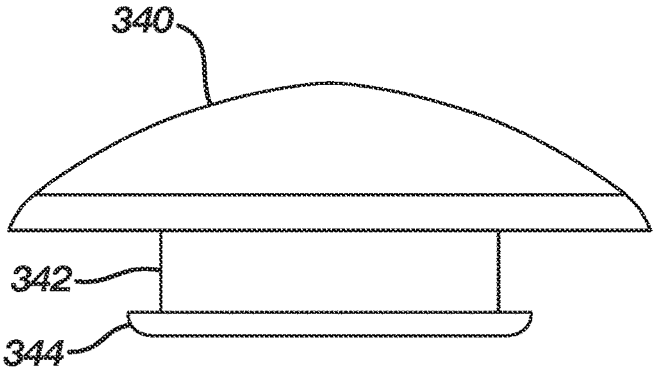
FIG. 7B is a schematic pictorial illustration showing a side view of an electrode, in accordance with another embodiment of the present invention.
Figure 7C:
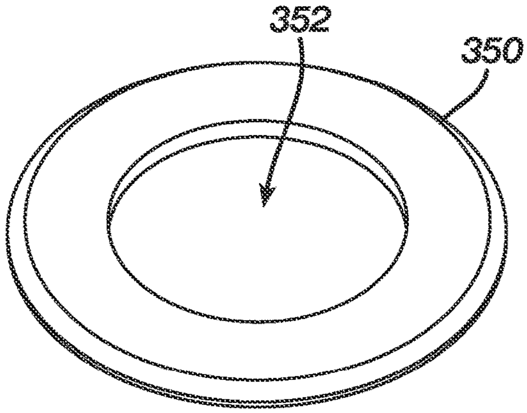
FIG. 7C is a schematic pictorial illustration showing a perspective view of a washer, in accordance with another embodiment of the present invention.

FIG. 7A is a schematic pictorial illustration showing a top view of the spine 214. As illustrated in FIG. 7A, the spine 214 can include a retainer ring 330 that can be a simple ring or circle formed in the spine 214. The retainer ring 330 can include an aperture 332 through which at least a portion of the electrode assembly 300 can pass or be positioned. As an example, and as illustrated in FIG. 7B, the electrode 340 can include a protrusion 342 that can be configured to extend through the aperture 332 of the retainer ring 330 when the electrode assembly 300 is attached to the spine 214. In this way, when the electrode 340 is engaged with the second washer 360, the electrode assembly 300 can be prevented from sliding along, or otherwise becoming disengaged with, the spine 214. As shown in FIG. 7B, the protrusion 342 of the electrode 340 can extend outwardly from the electrode 340 and include the swage fitting 344 as previously described. The protrusion 342 can be sized to fit in the aperture 332 of the retainer ring 330 as well as an aperture 352 of the first washer 350 and the aperture 362 of the second washer 360. The electrode 340 can be connected to a wire that passes through the back side of the electrode 340 proximate the swage fitting 344. The wire, for example, can be welding, crimped, soldered, or otherwise connected to the electrode by passing through the protrusion 342 and connecting to the interior surface of the electrode 340.

Figure 7D:
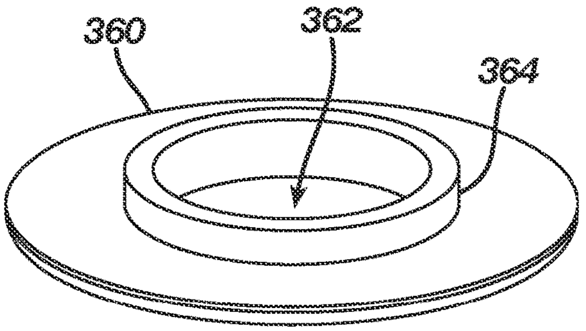
FIG. 7D is a schematic pictorial illustration showing a perspective view of another washer, in accordance with another embodiment of the present invention.
Figure 8A:
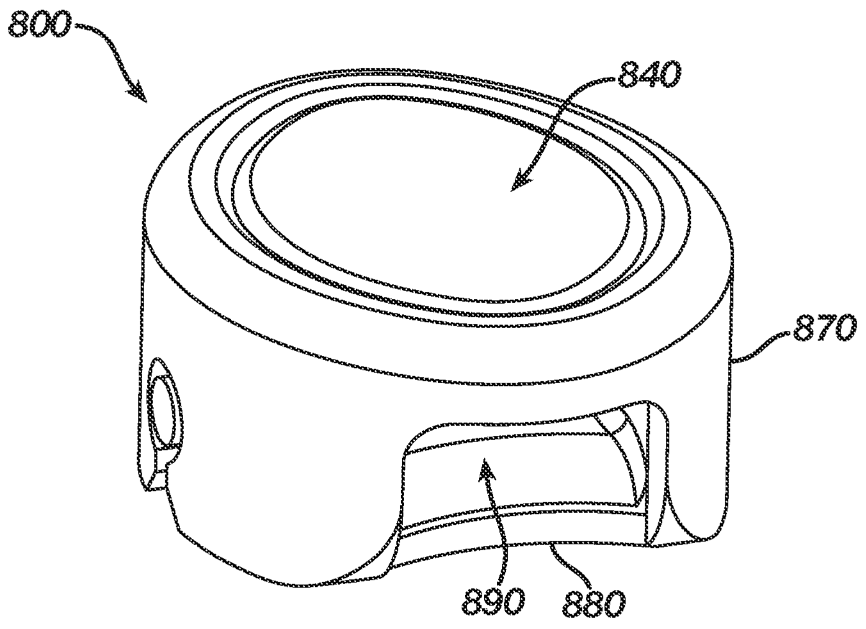
FIGS. 8A and 8B are schematic pictorial illustrations showing perspective views of an electrode assembly, in accordance with another embodiment of the present invention.
Figure 8B:
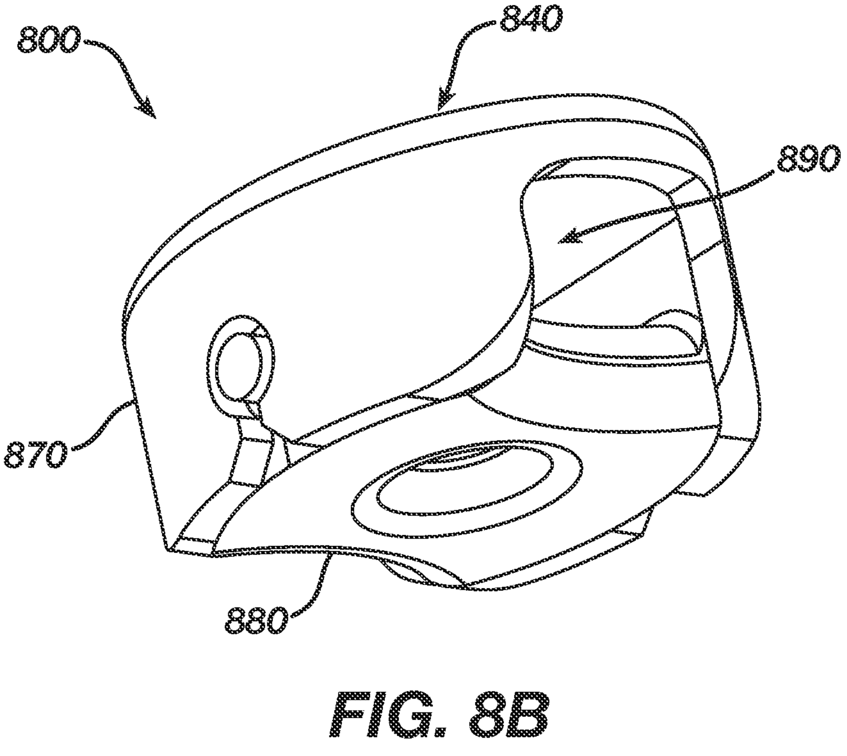

As shown in FIG. 7D, the second washer 360 can further include a lip 364 that can be configured to extend through the aperture 332 of the retainer ring 330. The lip 364 can also be sized to extend through the aperture 352 of the first washer 350 such that the electrode 340 is electrically isolated from the spine 214.

Although the electrode assembly 300 and its components are illustrated in FIGS. 4A-7D as having a generally cylindrical shape, one of skill in the art will appreciate that electrode assemblies 300 having other shapes are contemplated. For example, the electrode assembly 300 can comprise a generally rectangular, triangular, polygonal, oval, or any other suitable shape without departing from the scope of this disclosure. Furthermore, the retainer ring 330, the protrusion 342 of the electrode 340, the aperture 352 of the first washer 350, and the aperture 362 of the second washer 360 can each comprise a shape other than a generally circular shape as shown (i.e., a generally rectangular, triangular, polygonal, oval, or any other suitable shape). Thus, although the electrode assembly 300 is shown as described as having a particular shape and configuration, one of skill in the art will appreciate that the electrode assembly 300 can comprise various other shapes and configuration depending on the particular application without departing from the scope of this disclosure.

Turning now to FIGS. 8A-10D, another example electrode assembly 800 is shown and herein described. The electrode assembly 800 can be configured to perform a similar function as the electrode assembly 300 described herein. That is, the electrode assembly 800 can be configured to secure the electrode 840 to a spine 214 and the electrode 840 can be configured to deliver IRE ablation energy to cardiac tissue, among the other features herein described. The electrode assembly 800 can include an electrode 840, a first insulated housing portion 870, and a second insulated housing portion 880. The electrode 840 can include electrically conductive material as described in relation to the electrode 40 and the electrode 340 (e.g., gold, platinum, and palladium (and their respective alloys)). The first insulated housing portion 870 and the second insulated housing portion 880 can include a material that can electrically isolate the electrode 840 from the spine 214. For example, the first insulated housing portion 870 and the second insulated housing portion 880 can be made from a biocompatible, electrically insulative material such as Ultem, PEEK, liquid-crystaline polymer (Vectra/Zenite), polycarbonate, etc. The first insulated housing portion 870 and the second insulated housing portion 880 can include filler materials such as glass fiber having a concentration of approximately 2-30%. In this way, the first insulated housing portion 870 and the second insulated housing portion 880 can be configured to electrically isolate the electrode 840 from the spine 214 to prevent or reduce arcing between the electrode 840 and the spine 214.

The electrode assembly 800 can include a channel 890 through which at least a portion of the spine 214 can pass. For example, the channel 890 can be sized to at least partially receive the spine 214 such that the electrode assembly 800 can be secured to the spine 214 by clamping around the spine 214. For example, although not shown in FIG. 9, the spine 214 may be placed between the electrode 840 and the second insulated housing portion 880 such that when the electrode assembly 800 is pushed together to be assembled, the electrode assembly 800 can be secured around the spine 214. To further secure the electrode assembly 800 to the spine, a cross-sectional shape of the channel 890 can be slightly smaller than a cross-sectional shape of the spine 214. In this way, when the electrode assembly 800 is clamped together around the spine 214, the electrode assembly 800 forms a friction fit with the spine 214 to help prevent the electrode assembly 800 from sliding proximally and distally along a length of the spine 214.

Figure 9:
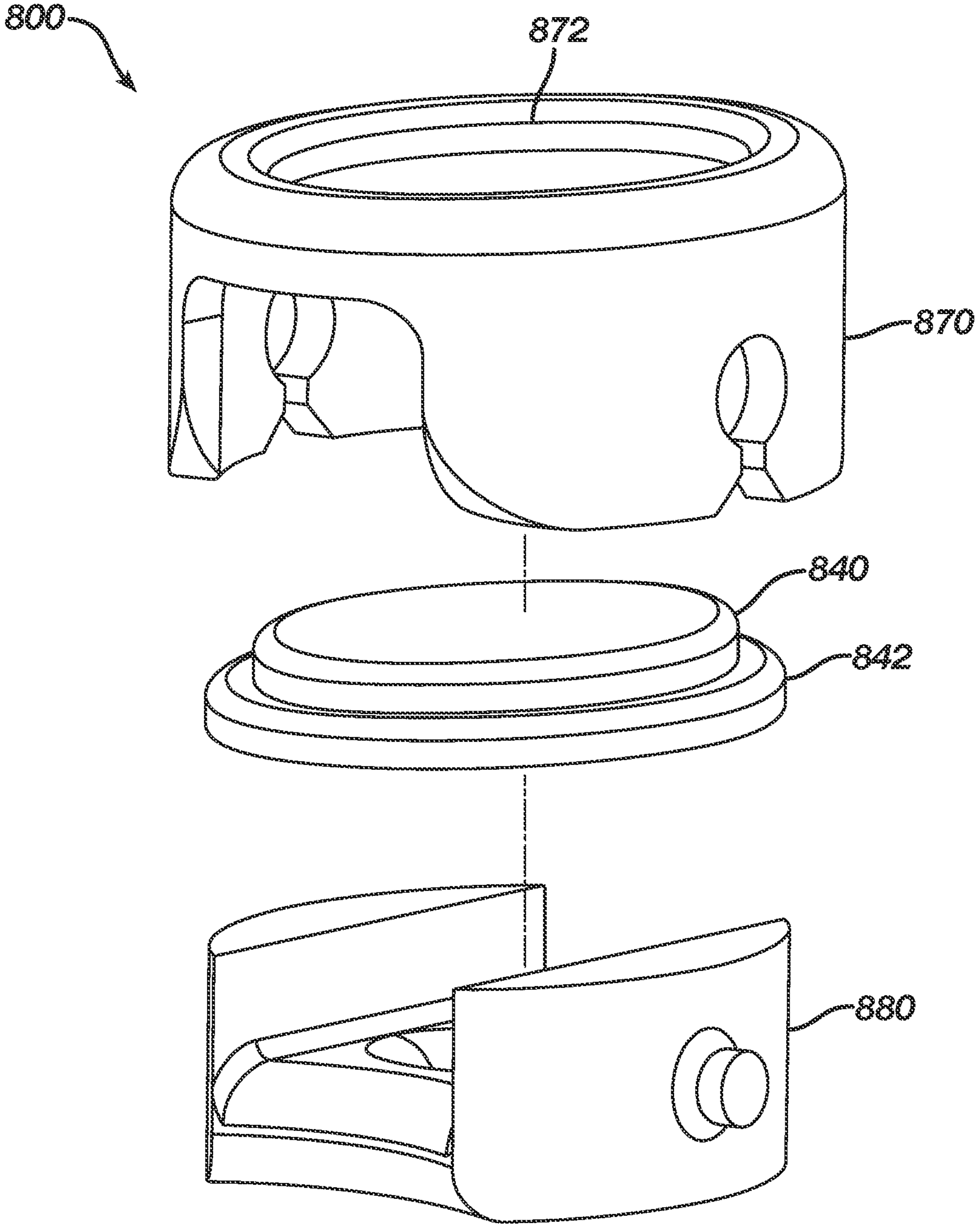
FIG. 9 is a schematic pictorial illustration showing an exploded view of an electrode assembly, in accordance with another embodiment of the present invention.

FIG. 9 is a schematic pictorial illustration showing an exploded view of the electrode assembly 800, in accordance with another embodiment of the present invention. As illustrated, the electrode 840 can include a base portion 842 that can extend outwardly from the electrode 840. The first insulated housing portion 870 can further include a rim 872 that can extend inwardly near the top portion of the first insulated housing portion 870. To help secure the electrode 840 in the electrode assembly 800, the base portion 842 can be sized to have an outer perimeter length that is larger than the inner perimeter length of the rim 872. Thus, when the electrode 840 placed between the first and second insulated housing portions 870, 880 and the first insulated housing portion 870 is secured to the second insulated housing portion 880, the electrode 840 can be secured in place because the base portion 842 and the rim 872 prevent the electrode 840 from falling out of the first insulated housing portion 870.

Figure 10A:
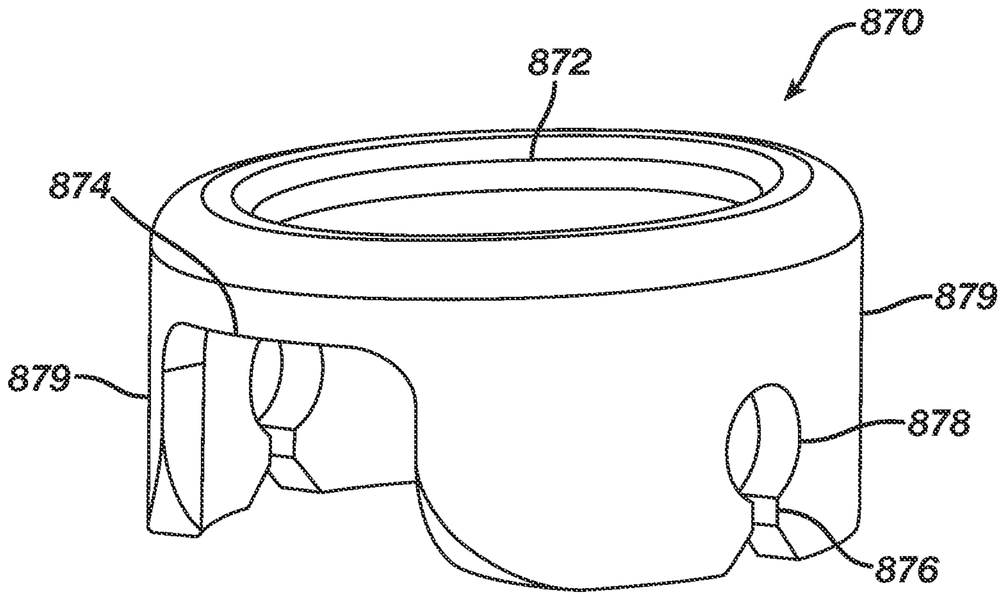
FIGS. 10A and 10B are schematic pictorial illustrations showing perspective views of a housing portion of an electrode assembly, in accordance with another embodiment of the present invention.
Figure 10B:
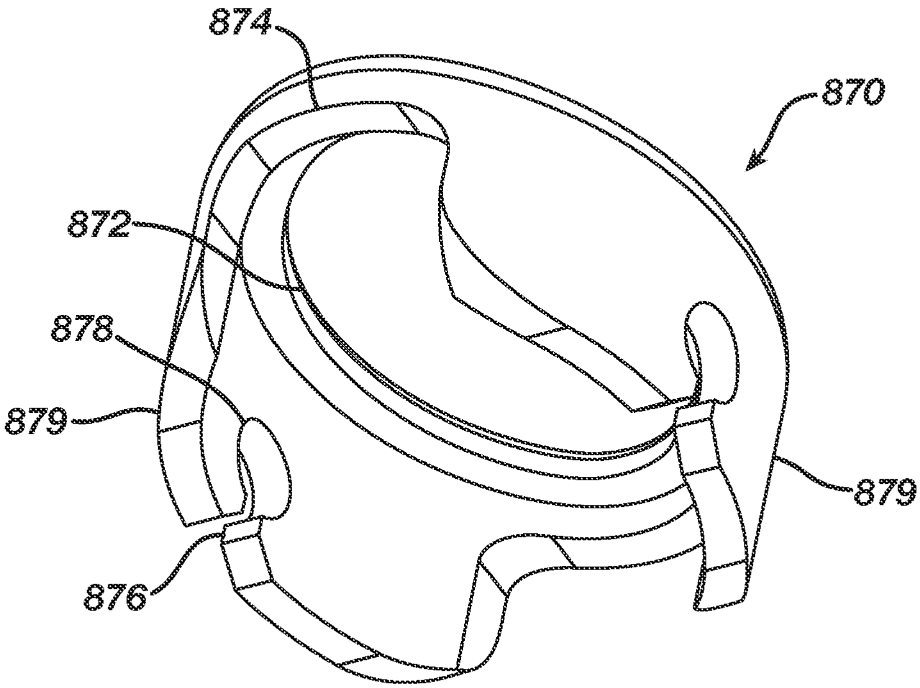

FIGS. 10A and 10B are schematic pictorial illustrations showing perspective views of the first insulated housing portion 870 of the electrode assembly 800. As illustrated, the first insulated housing portion 870 can include a channel opening 874 that can generally be a cut away portion of the first insulated housing portion 870 positioned between two sidewalls 879. The channel opening 874 can be sized to receive at least a portion of the spine 214. The channel opening 874 can include edges that are rounded to help reduce stress concentrations and the help reduce the likelihood that the first insulated housing portion 870 causes damage to the spine 214.

Figure 10C:
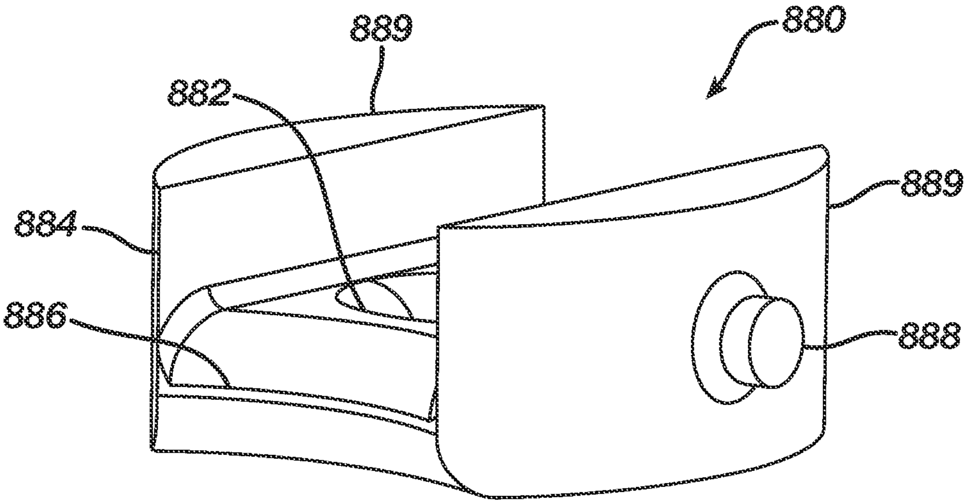
FIGS. 10C and 10D are schematic pictorial illustrations showing perspective views of another housing portion of an electrode assembly, in accordance with another embodiment of the present invention.
Figure 10D:
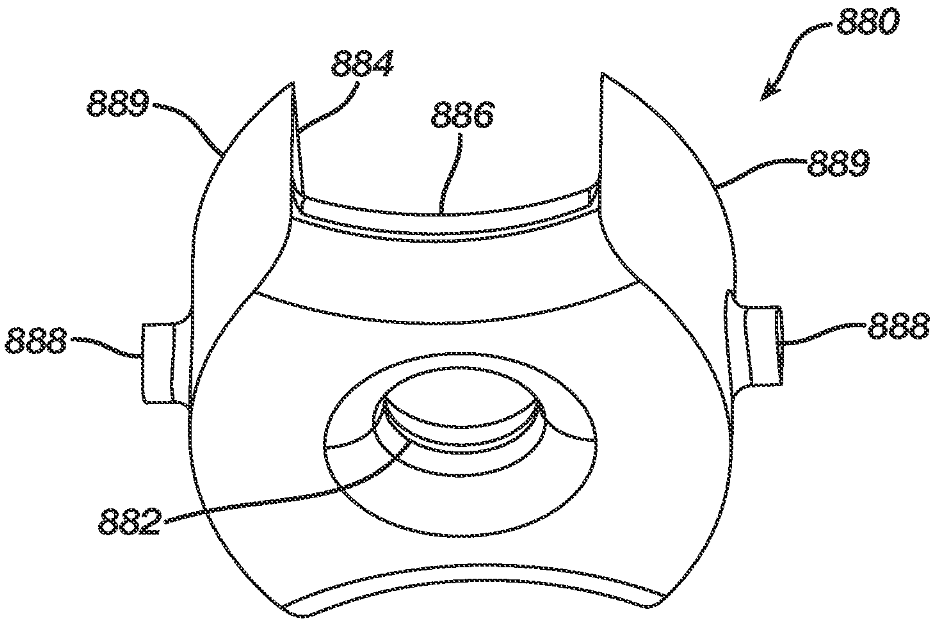

The first insulated housing portion 870 can further include a female connector 878 that is sized to receive a corresponding male connector 888 of the second insulated housing portion 880 (as shown and described in relation to FIGS. 10C and 10D). The female connector 878 can be positioned in or on a sidewall 879 of the first insulated housing portion 870 such that the female connector 878 can be positioned near a side of the spine 214 when the electrode assembly 800 is secured to the spine 214. The female connector 878 can include a narrow portion 876 that can be configured to allow the male connector 888 to be pushed into the female connector 878 but prevent the male connector 888 from being removed from the female connector 878 once assembled. For example, the narrow portion 876 can be sloped to a point that comprises a distance between opposing edges of the narrow portion 876 that is smaller than a diameter of the male connector 888. Thus, the narrow portion 876 can allow the male connector 888 to be slid through the narrow portion 876 in a first direction but prevent the male connector 888 from sliding through the narrow portion 876 in a second direction. The first insulated housing portion 870, the second insulated housing portion 880, or both, can be made from a resilient material to allow the narrow portion 876, the male connector 888, or both to deflect when the male connector 888 is pushed into the female connector 878.

FIGS. 10C and 10D are schematic pictorial illustrations showing perspective views of the second insulated housing portion 880 of the electrode assembly 800. As described previously, the second insulated housing portion 880 can include a male connector 888 that can protrude from the second insulated housing portion 880 and be configured to interlock with the female connector 878 of the first insulated housing portion 870. The second insulated housing portion 880 can further include channel portion 884 that can be sized to receive the spine 214 similar to the channel portion 874 of the first insulated housing portion 870. The channel portion 884 can be configured to align with the channel portion 874 such that the spine 214 can be positioned between the first insulated housing portion 870 and the second insulated housing portion 880 when assembled.

The channel portion 884 can include a rounded lip 886 that can be positioned proximate an outer edge of the channel portion 884 to help reduce stress concentrations and reduce the likelihood that the second insulated housing portion 880 damages the spine 214. The rounded lip 886 can include a rounded edge and be a generally concave shape such that the rounded lip 886 can permit the spine 214 to bend when transitioned between an expanded form and a collapsed form.

The second insulated housing portion 880 can include a wire aperture 882 that can be configured to receive a wire of the electrode assembly 800. For example, the wire can be disposed along the spine 214 and then pass through the wire aperture 882 and be electrically connected to the electrode 840. The wire can be welding, soldered, crimped, or otherwise connected to the electrode 840. The wire aperture 882 can include rounded edges to help reduce stress concentrations and reduce the likelihood that the second insulated housing portion 880 damages the wire. Alternatively, or in addition, the wire aperture 882 can be used for electrode 840 alignment. For example, the electrode 840 may have a pin-like emboss that would insert through an aperture included in the first insulated housing portion 870 and second insulated housing portion 880.

Although described as the first insulated housing portion 870 having the female connector 878 and the second insulated housing portion 880 having the male connector 888, one of skill in the art will appreciate that the two can be switched. In other words, the first insulated housing portion 870 can have the male connector 888 while the second insulated housing portion 880 can have a female connector 878 without departing from the scope of this disclosure. Furthermore, the electrode assembly 800 can have any number of female connectors 878 and male connectors 888 as would be suitable for the particular application.

Although the electrode assembly 800 and its components are illustrated in FIGS. 8A-10D as having a particular shape, one of skill in the art will appreciate that electrode assemblies 300 having other shapes are contemplated. For example, the electrode assembly 300 can comprise a generally circular, rectangular, triangular, polygonal, oval, or any other suitable shape without departing from the scope of this disclosure.

Figure 11A:
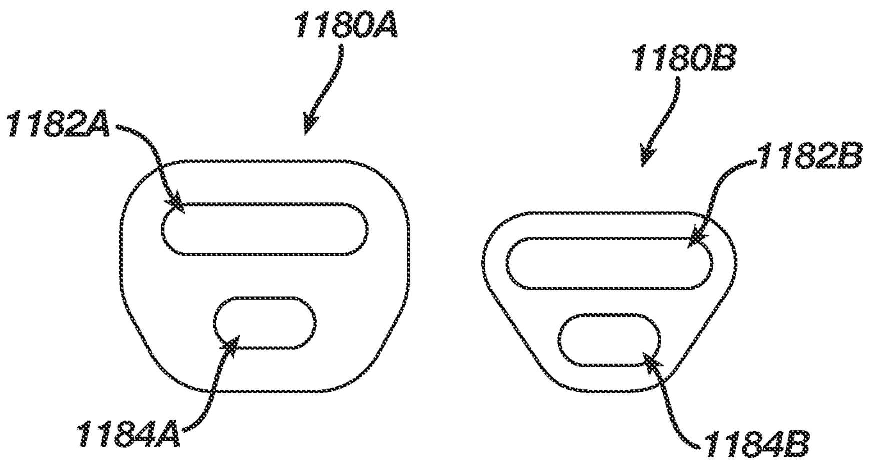
FIGS. 11A and 11B are schematic pictorial illustrations showing various insulative jackets of a given medical device, in accordance with embodiments of the present invention.
Figure 11B:
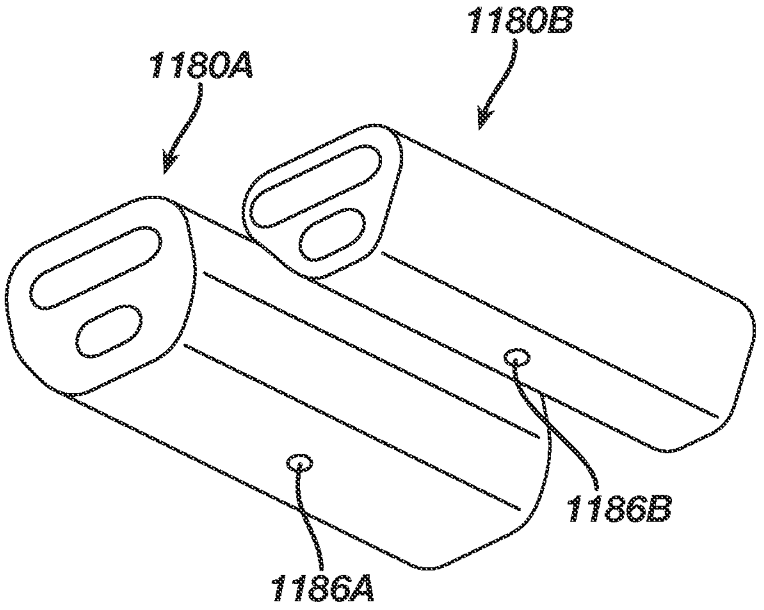

FIGS. 11A and 11B are schematic pictorial illustrations showing various insulative jackets 1180A, 1180B of a given medical device 22, in accordance with embodiments of the present invention. FIG. 11A is a front view while FIG. 11B is a perspective view of the insulative jackets 1180A, 1180B. The insulative jackets 1180A, 1180B can be made from a biocompatible, electrically insulative material such as polyamide-polyether (Pebax) copolymers, polyethelyene terephthalate (PET), urethanes, polyimide, parylene, silicone, etc. The insulative jackets 1180A, 1180B can further include a filler material such as PTFE, boron nitride, etc. The insulative jacket 1180A, 1180B can help to insulate a strut and/or wires passing through the insulative jacket 1180A, 1180B from the electrode 40 to prevent arcing from the electrode 40, 340, and/or 840 to the strut and/or wires passing through the insulative jacket 1180A, 1180B.

As illustrated in FIGS. 11A and 11B, the insulative jacket 1180A, 1180B, can include a cross-sectional shape that is substantially trapezoidal. The insulative jacket may consist of a single lumen or multi-lumen configuration. Multi-lumen jackets may be configured such that the alloy frame and wires share a single lumen while the second lumen may be used for irrigation. The alloy frame and wires may occupy separate lumens, also, as described. For these designs, the insulative jackets may be continuous (individual sleeves extending from proximal to distal end of each alloy frame strut), segmented (bridging between electrode gaps), or a combination of both. Furthermore, the insulative jacket 1180A, 1180B can include a first lumen 1182A, 1182B and a second lumen 1184A, 1184B. The first lumen 1182A, 1182B can be configured to receive a strut while the second lumen 1184A, 1184B can be configured to receive a wire, or vice-versa. In other examples, the first lumen 1182A, 1182B and the second lumen 1184A, 1184B can each be configured to receive one or more wires that can be connected to one or more electrodes 40. Furthermore, as illustrated in FIG. 10B, the insulative jacket 1180A, 1180B can include an aperture 1186A, 1186B through which a wire can be electrically connected to the electrode 40. Although illustrated in FIG. 10B as being proximate a bottom of the insulative jacket 1180A, 1180B, the aperture 1186A, 1186B can be positioned proximate a top or side of the insulative jacket 1180A, 1180B. Furthermore, the insulative jacket 1180A, 1180B can include multiple apertures 1186A, 1186B with each aperture being disposed on the same side of the insulative jacket (i.e., top, bottom, left, right) or on different sides of the insulative jacket depending on the application.

Figure 12A:
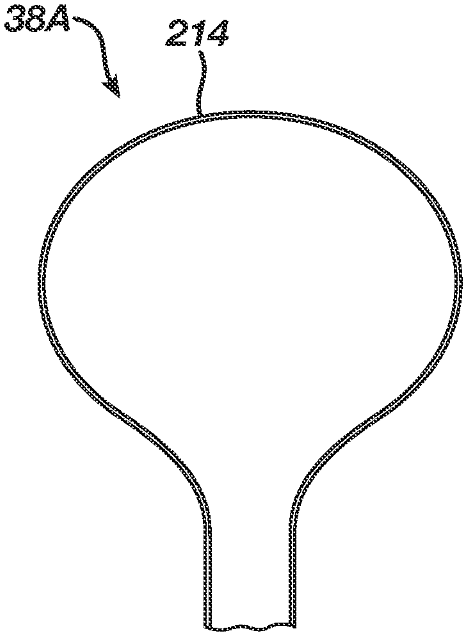
FIGS. 12A and 12B are schematic pictorial illustrations showing a side view of a spine of a given medical device, in accordance with embodiments of the present invention.
Figure 12B:
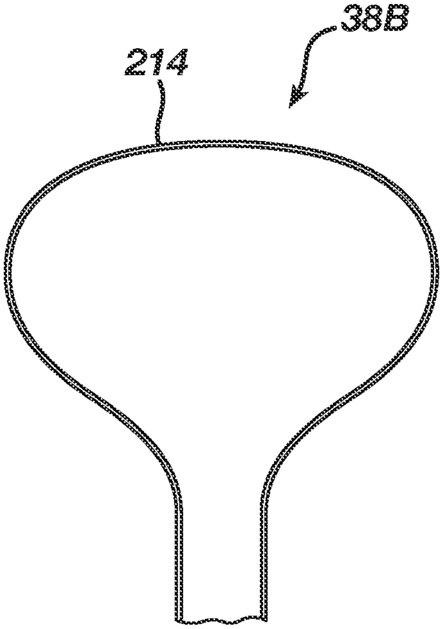

FIGS. 12A and 12B are schematic pictorial illustrations showing a side view of a spine 214 of a given medical device 22, in accordance with embodiments of the present invention. As will be appreciated, the spine 214 illustrated in FIGS. 12A and 12B is a single spine 214 and can be representative of the plurality of spines 214 of the basket assembly 38 described herein. In other words, the plurality of spines 214 forming the basket assembly 38 can each be configured to form the same or similar shape when in the expanded form such that the plurality of spines 214 together form a desired shape. To illustrate, the spine 214 as shown in FIG. 12A can be configured to form an approximately circular shape when in the expanded form. Thus, when combined with other spines 214 to form the basket assembly 38, the plurality of spines 214 can be configured to form an approximately spherical shape when the basket assembly 38 is in the expanded form. As another example, the spine 214 shown in FIG. 12B can be configured to form an approximately elliptical shape when in the expanded form. Thus, when combined with other spines 214 to form the basket assembly 38, the plurality of spines 214 can be configured to form an approximately oblate-spheroid shape when the basket assembly 38 is in the expanded form. Although not every variation of shape is shown or described herein, one skilled in the art will appreciate that the spines 214 can be further configured to form other various shapes as would be suitable for the particular application. Further, the medical device 22 can include one or more spines of alternative shapes which can form a shape having a profile with a periphery shaped similar to the spine 214 illustrated in FIG. 12A or 12B.

By including spines 214 configured to form various shapes when in the expanded form, the basket assembly 38 can be configured to position the various electrodes 40 attached to the spines 214 at various locations, with each location being nearer or farther from the distal end of the flexible insertion tube 30. For example, an electrode 40 attached to the spine 214 illustrated in FIG. 12A near the middle of the spine 214 would be farther from the distal end of the flexible insertion tube 30 than the spine 214 illustrated in FIG. 12B when the basket assembly 38 is in the expanded form.

Figure 13A:
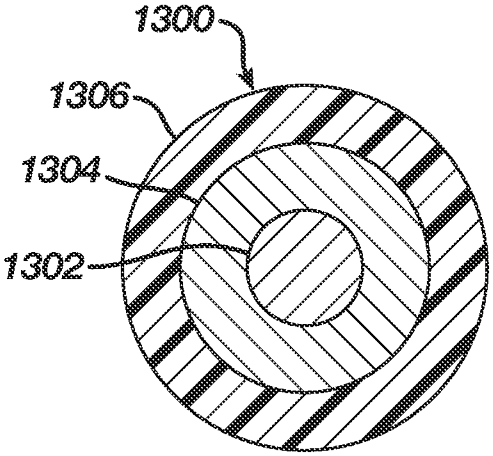
FIGS. 13A and 13B are schematic pictorial illustrations showing cross-sectional views of a given wire of a medical probe, in accordance with an embodiment of the present invention.
Figure 13B:
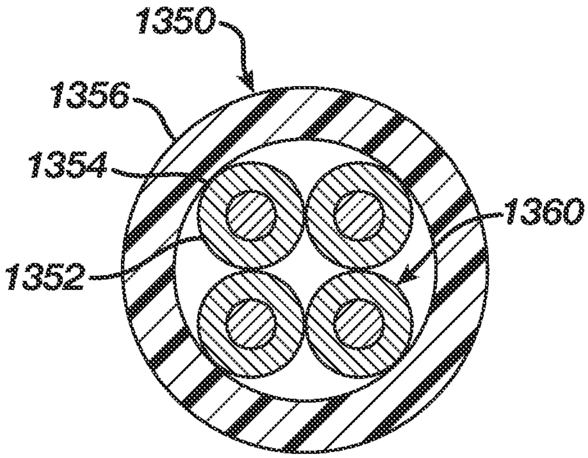

FIGS. 13A and 13B are schematic pictorial illustrations showing cross-sectional views of a given wire 1300, 1350 that can be connected to a given electrode 40, 340, 840, in accordance with an embodiment of the present invention. FIG. 13A illustrates a solid core wire 1300. FIG. 13B illustrates a stranded wire 1350. Each wire 1300, 1350 can extend through at least a portion of the tubular shaft 84. The solid core wire 1300 can include an electrically conductive core material 1302 and an electrically conductive cover material 1304 circumscribing electrically conductive core material 1302. Likewise, the stranded wire 1350 can include strands each including an electrically conductive core material 1352 and an electrically conductive cover material 1354 circumscribing the electrically conductive core material 1352. Each wire 1300, 1350 can include an insulative jacket 1306 circumscribing the conductors. The wires 1300, 1350 can be configured to withstand a voltage difference of adjacent wires sufficient to deliver IRE pulses. Preferably, the wires 1300, 1350 can withstand at least 900V, and more preferably at least 1,800V between adjacent wires. To reduce likelihood of dielectric breakdown between conductors of adjacent wires, the electrically conductive cover material 1304, 1354 can have a lower electrical conductivity compared to the core material 1302, 1352.

The insulative jacket 1306 can be configured to have a temperature rating between 150 and 200 degrees Centigrade so that the electrically insulative jacket 1306 melts or degrades (e.g., chars and crumbles) during soldering of the wire 1300 to the electrodes 40 (e.g., at a temperature of 300 degrees Centigrade) and therefore the insulative jacket 1306 of the wire 1300 does not need to be mechanically stripped. In other examples, the insulative jacket 1306 can have a temperature rating greater than 200 degrees Centigrade to prevent the electrically insulating material 1302 melting or degrading (e.g., charring and crumbling) during manufacture of the medical probe 22 and/or during use. The insulative jacket 1306 can be mechanically stripped from the wire 1300 prior to the wires 1300 being electrically connected to the electrodes 40.

Figure 14:
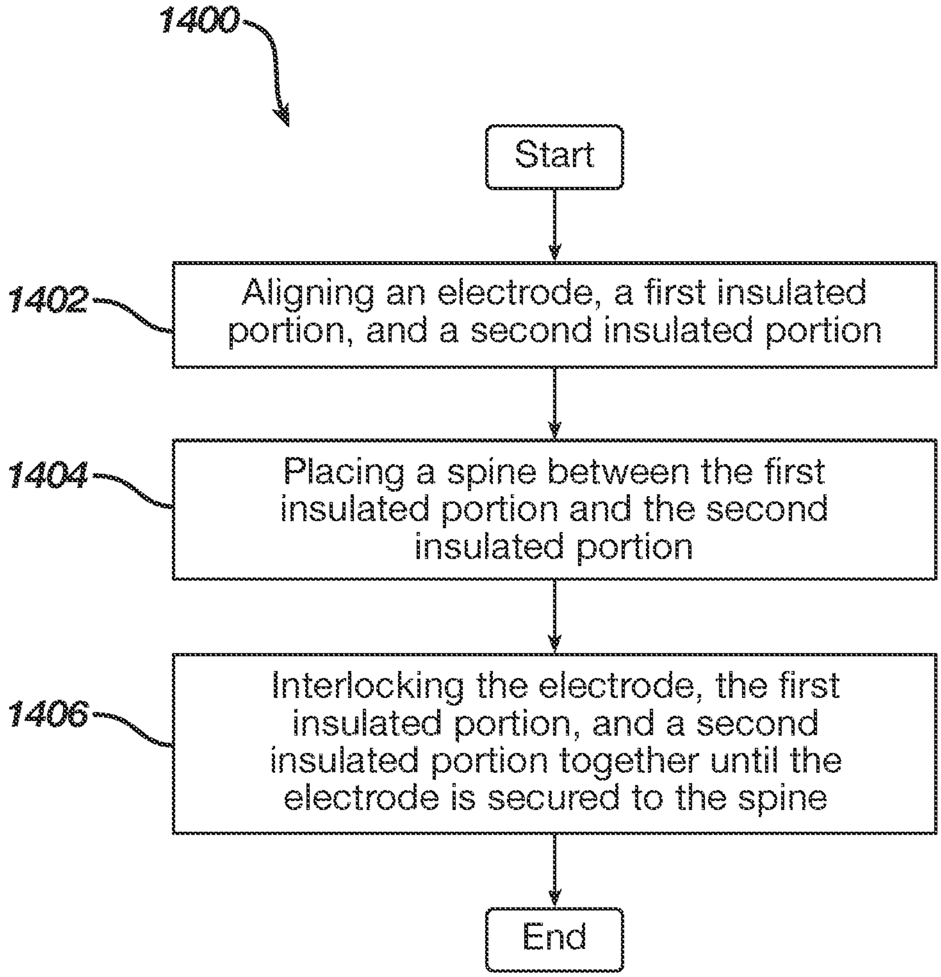
FIG. 14 is a flowchart illustrating a method of assembling a basket assembly, in accordance with an embodiment of the present invention.

FIG. 14 is a flowchart illustrating a method 1400 of manufacturing a basket assembly 38, in accordance with an embodiment of the present invention. The method 1400 can include aligning 1402 a spine 214 of an expandable basket assembly 38 with a first insulated portion, and a second insulated portion. For example, as described herein, the method 1400 can include aligning 1402 a spine 214 with an electrode 340, a first washer 350, and a second wash 360. As another example, as described herein, the method 1400 can include aligning 1402 a spine 214 with an electrode 840, a first insulated housing portion 870, and a second insulated housing portion 880.

The method 1400 can further include placing 1404 the spine 214 between the first insulated portion and the second insulated portion. For example, as described herein, the spine 214 can be positioned between the first washer 350 and the second washer 360. As another example, as described herein, the spine 214 can be placed between the first insulated housing portion 870 and the second insulated housing portion 880 with the electrode 840 being disposed between the spine 214 and the first insulated housing portion 870.

The method 1400 can further include interlocking 1406 the electrode 340, 840, the first insulated portion (i.e., the first washer 350 or the first insulated housing portion 870), and the second insulated portion (i.e., the second washer 360 or the second insulated housing portion 880) together until the electrode is secured to the spine 214. For example, the method 1400 can include interlocking the electrode 340, the first washer 350, and the second washer 360 together until the electrode assembly 300 is secured in place by the swage fitting 344 engaging with the second washer 360. As another example, the method 1400 can include pushing the first insulated housing portion 870 together with the second insulated housing portion 880 until the male connectors 888 engages with the female connector 878 and the electrode assembly 800 is secured to the spine 214.

As will be appreciated by one skilled in the art, the method 1400 can include any of the various features of the disclosed technology described herein and can be varied depending on the particular configuration. Thus, the method 1400 should not be construed as limited to the particular steps and order of steps explicitly described herein.

The disclosed technology described herein can be further understood according to the following clauses:

Clause 1: A medical probe, comprising: a tubular shaft having a proximal end and a distal end, the tubular shaft extending along a longitudinal axis; and an expandable basket assembly coupled to the distal end of the tubular shaft, the basket assembly comprising: at least one spine extending along the longitudinal axis and configured to bow radially outward from the longitudinal axis when the expandable basket assembly is transitioned from a collapsed form to an expanded form; and a plurality of electrode assemblies, each electrode assembly of the plurality of electrode assemblies being attached to the at least one spine and comprising: an electrode; a first electrically insulating portion electrically isolating the electrode from the at least one spine; and a second electrically insulating portion electrically isolating the electrode from the at least one spine, the electrode, the first electrically insulating portion, and the second electrically insulating portion being interlocked onto the at least one spine such that the plurality of electrode assemblies are prevented from sliding proximally or distally along a length of the at least one spine.

Clause 2: The medical probe according to Clause 1, wherein the at least one spine comprises a retainer ring onto which a respective electrode assembly of the plurality of electrode assemblies is interlocked.

Clause 3: The medical probe according to Clause 1 or Clause 2, wherein the electrode comprises a protrusion configured to interlock with the second electrically insulating portion.

Clause 4: The medical probe according to Clause 3, wherein the protrusion is extending through the retainer ring, thereby preventing the electrode assembly from sliding along the length of the at least one spine.

Clause 5: The medical probe according to Clause 4, wherein the protrusion further comprises a swage fitting.

Clause 6: The medical probe according to any of Clauses 1-4, wherein: the first electrically insulating portion comprises a first washer; and the second electrically insulating portion comprises a second washer.

Clause 7: The medical probe according to Clause 6, wherein the first washer and the second washer are configured to prevent the electrode from contacting the at least one spine and to electrically isolate the electrode from the at least one spine.

Clause 8: The medical probe according to Clause 7, wherein the second washer comprises a lip configured to extend inwardly into the retainer ring to prevent the electrode from contacting the at least one spine.

Clause 9: The medical probe according to Clause 1, wherein: the first electrically insulating portion comprises a first housing portion; and the second electrically insulating portion comprises a second housing portion.

Clause 10: The medical probe according to Clause 9, wherein the first housing portion and the second housing portion are configured to interlock to secure the electrode to the at least one spine.

Clause 11: The medical probe according to Clause 10, wherein: the second housing portion comprises a male connector; and the first housing portion comprises a female connector configured receive the male connector and facilitate the first housing portion to interlock with the second housing portion.

Clause 12: The medical probe according to any of Clauses 9-11, the first housing portion comprising a rim configured to receive the electrode.

Clause 13: The medical probe according to Clause 12, the electrode further comprising a base portion configured to retain the electrode in the rim of the first housing portion.

Clause 14: The medical probe according to Clause 13, wherein the base portion comprises an outer perimeter length that is greater than an inner perimeter length of the rim.

Clause 15: The medical probe according to any of Clauses 1-14, wherein the electrode is electrically connected to a wire of the medical probe.

Clause 16: The medical probe according to Clause 15, wherein at least a portion of the wire comprises an electrically conductive core material comprising a first electrical conductivity, an electrically conductive cover material comprising a second electrical conductivity less than the first electrical conductivity, the electrically conductive cover material circumscribing the electrically conductive core material, and an insulative jacket circumscribing the electrically conductive cover material.

Cluse 17: The medical probe according to any of Clauses 15 or 16, wherein at least a portion of the wire comprises a plurality of strands and an insulative jacket circumscribing the plurality of the strands, and wherein each strand of the plurality of strands respectively comprises an electrically conductive core material comprising a first electrical conductivity and an electrically conductive cover material comprising a second electrical conductivity less than the first electrical conductivity, the electrically conductive cover material circumscribing the electrically conductive core material.

Clause 18: The medical probe according to any of Clauses 1-17, wherein the at least one spine comprises nitinol.

Clause 19: The medical probe according to any of Clauses 1-18, wherein the at least one spine comprises cobalt chromium.

Clause 20: The medical probe according to any of Clauses 1-19, wherein the plurality of electrodes is configured to deliver electrical pulses for irreversible electroporation, the pulses having a peak voltage of at least 900 volts (V).

Clause 21: The medical probe according to any of Clauses 1-20, wherein the at least one spine is configured to form an approximately spherically-shaped basket assembly.

Clause 22: The medical probe according to any of Clauses 1-20, wherein the at least one spine is configured form an approximately oblate-spheroid basket assembly.

Clause 23: The medical probe according to any of Clause 1-22, wherein the at least one spine further comprises an electrically insulative jacket, the electrically insulative jacket comprising a first lumen and a second lumen, the first lumen configured to receive a first wire and the second lumen configured to receive a second wire.

Clause 24: The medical probe according to any of Clause 23, wherein a cross-sectional shape of the electrically insulative jacket comprises a substantially trapezoidal shape.

Clause 25: The medical probe according to any of Clauses 1-24, further comprising irrigation openings configured to deliver an irrigation fluid to the plurality of electrodes.

Clause 26: A method of constructing a medical probe, the method comprising: aligning an electrode, a first insulated portion, and a second insulated portion; placing a spine of a basket catheter between the first insulated portion and the second insulated portion; and interlocking the electrode, the first insulated portion, and the second insulated portion together to secure the electrode to the spine such that the first insulated portion and the second insulated portion electrically isolate the electrode from the spine and such that the electrode, the first insulated portion, and the second insulated portion are prevented from sliding proximally or distally along a length of the spine.

Clause 27: The method according to Clause 26, wherein interlocking the electrode, the first insulated portion, and the second insulated portion together comprises interlocking a portion of at least one of the electrode, the first insulated portion, and the second insulated portion through an aperture of a retainer ring of the spine.

Clause 28: The method according to Clause 27, further comprising aligning the electrode, the first insulated portion, and the second insulated portion with the retainer ring.

Clause 29: The method according to Clause 28, wherein interlocking the electrode, the first insulated portion, and the second insulated portion together comprises interlocking a protrusion of the electrode with the second insulated portion.

Clause 30: The method according to Clause 29, further comprising forming a swage fitting on the protrusion to cause the electrode to interlock with the second insulated portion.

Clause 31: The method according to Clause 29, wherein interlocking the electrode, the first insulated portion, and the second insulated portion together comprises extending the protrusion through the retainer ring thereby preventing the electrode from sliding proximally or distally along the length of the spine.

Clause 32: The method according to any of Clauses 26-31, wherein: the first insulated portion comprises a first insulated washer; and the second insulated portion comprises a second insulated washer.

Clause 33: The method according to Clause 32, further comprising:

positioning the first insulated washer and the second insulated washer so that the electrode is electrically isolated from the spine.

Clause 34: The method according to Clause 32, wherein interlocking the electrode, the first insulated portion, and the second insulated portion together comprises extending a lip of the second insulated washer inwardly into the retainer ring thereby preventing the electrode from contacting the spine.

Clause 35: The method according to Clause 26, wherein: the first insulated portion comprises a first insulated housing portion; and the second insulated portion comprises a second insulated housing portion.

Clause 36: The method according to Clause 35, wherein interlocking the electrode, the first insulated portion, and the second insulated portion together comprises interlocking the first insulated housing portion and the second insulated housing portion to thereby secure the electrode to the spine.

Clause 37: The method according to Clause 36, wherein: the second insulated housing portion comprises a male connector; and the first insulated housing portion comprises a female connector configured receive the male connector and facilitate the first insulated housing portion to interlock with the second insulated housing portion.

Clause 38: The method according to any of Clauses 35-37, the first insulated housing portion comprising a rim configured to receive the electrode.

Clause 39: The method according to Clause 38, wherein interlocking the electrode, the first insulated portion, and the second insulated portion together comprises retaining a base portion of the electrode in the rim.

Clause 40: The method according to Clause 39, wherein the base portion comprises an outer perimeter length that is greater than an inner perimeter length of the rim.

Clause 41: The method according to any of Clauses 26-40, further comprising electrically connecting the electrode to a wire of the medical probe.

Clause 42: The method according to Clause 41, wherein at least a portion of the wire comprises an electrically conductive core material comprising a first electrical conductivity, an electrically conductive cover material comprising a second electrical conductivity less than the first electrical conductivity, the electrically conductive cover material circumscribing the electrically conductive core material, and an insulative jacket circumscribing the electrically conductive cover material.

Clause 43: The method according to Clauses 41 or 42, wherein at least a portion of the wire comprises a plurality of strands and an insulative jacket circumscribing the plurality of the strands, and wherein each strand of the plurality of strands respectively comprises an electrically conductive core material comprising a first electrical conductivity and an electrically conductive cover material comprising a second electrical conductivity less than the first electrical conductivity, the electrically conductive cover material circumscribing the electrically conductive core material.

Clause 44: The method according to any of Clauses 26-43, wherein the spine comprises nitinol.

Clause 45: The method according to any of Clauses 26-43, wherein the spine comprises cobalt chromium.

Clause 46: The method according to any of Clauses 26-45, wherein the electrode is configured to deliver electrical pulses for irreversible electroporation, the pulses having a peak voltage of at least 900 volts (V).

Clause 47: The method according to any of Clauses 26-46, wherein the spine is configured to form an approximately spherically-shaped basket assembly.

Clause 48: The method according to any of Clauses 26-46, wherein the spine is configured form an approximately oblate-spheroid basket assembly.

Clause 49: The method according to any of Clause 26-48, wherein the spine further comprises an electrically insulative jacket, the electrically insulative jacket comprising a first lumen and a second lumen, the first lumen configured to receive a first wire and the second lumen configured to receive a second wire.

Clause 50: The method according to any of Clause 49, wherein the electrically insulative jacket comprises a substantially trapezoidal shape.

Clause 51: The method according to any of Clauses 26-50, further comprising configuring irrigation openings to deliver an irrigation fluid to the electrode.

The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A medical probe, comprising:

a tubular shaft having a proximal end and a distal end, the tubular shaft extending along a longitudinal axis; and an expandable basket assembly coupled to the distal end of the tubular shaft, the basket assembly comprising:

at least one spine extending along the longitudinal axis and configured to bow radially outward from the longitudinal axis when the expandable basket assembly is transitioned from a collapsed form to an expanded form; and a plurality of electrode assemblies, each electrode assembly of the plurality of electrode assemblies being attached to one respective spine of the at least one spine and comprising:

an electrode;

a first electrically insulating portion electrically isolating the electrode from the one respective spine; and a second electrically insulating portion electrically isolating the electrode from the one respective spine, the second electrically insulating portion being spaced apart from another second electrically insulating portion of another electrode assembly of the plurality of electrode assemblies along a length of the one respective spine;

the electrode, the first electrically insulating portion, and the second electrically insulating portion being interlocked onto the one respective spine such that the plurality of electrode assemblies are prevented from sliding proximally or distally along the length of the one respective spine, a first portion of each electrode assembly in the plurality of electrode assemblies being on a first side of the one respective spine, and a second portion of each electrode assembly in the plurality of electrode assemblies being on a second side of the one respective spine opposite the first side.

2. The medical probe according to claim 1, wherein the at least one spine comprises a retainer ring onto which a respective electrode assembly of the plurality of electrode assemblies is interlocked.

3. The medical probe according to claim 2, wherein the electrode comprises a protrusion configured to interlock with the second electrically insulating portion.

4. The medical probe according to claim 3, wherein the protrusion is extending through the retainer ring, thereby preventing the electrode assembly from sliding along the length of the at least one spine.

5. The medical probe according to claim 4, wherein the protrusion further comprises a swage fitting.

6. The medical probe according to claim 1, wherein:

the first electrically insulating portion comprises a first washer; and the second electrically insulating portion comprises a second washer.

7. The medical probe according to claim 6, wherein the first washer and the second washer are configured to prevent the electrode from contacting the at least one spine and to electrically isolate the electrode from the at least one spine.

8. The medical probe according to claim 7, wherein the second washer comprises a lip configured to extend inwardly into a retainer ring of the at least one spine to prevent the electrode from contacting the at least one spine.

9. The medical probe according to claim 1, wherein:

the first electrically insulating portion comprises a first housing portion; and the second electrically insulating portion comprises a second housing portion.

10. The medical probe according to claim 9, wherein the first housing portion and the second housing portion are configured to interlock to secure the electrode to the at least one spine.

11. The medical probe according to claim 10, wherein:

the second housing portion comprises a male connector; and the first housing portion comprises a female connector configured to receive the male connector and facilitate the first housing portion to interlock with the second housing portion.

12. The medical probe according to claim 9, the first housing portion comprising a rim configured to receive the electrode.

13. The medical probe according to claim 12, the electrode further comprising a base portion configured to retain the electrode in the rim of the first housing portion.

14. The medical probe according to claim 13, wherein the base portion comprises an outer perimeter length that is greater than an inner perimeter length of the rim.

15. A method of constructing a medical probe, the method comprising:

aligning an electrode, a first insulated portion, and a second insulated portion;

placing a spine of a basket catheter between the first insulated portion and the second insulated portion, the spine defining an aperture; and interlocking the electrode, the first insulated portion, and the second insulated portion together to define an electrode assembly that extends at least partially through the aperture to secure the electrode to the spine such that the first insulated portion and the second insulated portion electrically isolate the electrode from the spine and such that the electrode, the first insulated portion, and the second insulated portion are prevented from sliding proximally or distally along a length of the spine, with a first portion of the electrode assembly on a first side of the spine, and a second portion of the electrode assembly on a second side of the spine opposite the first side.

16. The method according to claim 15, the aperture being defined through a retainer ring of the spine.

17. The method according to claim 16, further comprising aligning the electrode, the first insulated portion, and the second insulated portion with the retainer ring.

18. The method according to claim 17, wherein interlocking the electrode, the first insulated portion, and the second insulated portion together comprises interlocking a protrusion of the electrode with the second insulated portion.

* * * * *